(12) United States Patent
Hoerl

(10) Patent No.: US 8,683,024 B2
(45) Date of Patent: Mar. 25, 2014

(54) SYSTEM FOR VIDEO DIGITIZATION AND IMAGE CORRECTION FOR USE WITH A COMPUTER MANAGEMENT SYSTEM

(75) Inventor: David Hoerl, Warren, NJ (US)

(73) Assignee: RIIP, Inc., Wilmington, DE (US)

( * ) Notice: Subject to any disclaimer, the term of this patent is extended or adjusted under 35 U.S.C. 154(b) by 180 days.

(21) Appl. No.: 10/724,002

(22) Filed: Nov. 26, 2003

(65) Prior Publication Data
US 2005/0114894 A1 May 26, 2005

(51) Int. Cl.
*G06F 15/173* (2006.01)

(52) U.S. Cl.
USPC ........... 709/223; 709/203; 709/217; 713/189; 726/26; 345/1.3; 345/87; 345/99; 348/341; 348/360

(58) Field of Classification Search
USPC ......... 709/203–204, 223–224, 231, 246, 217; 345/1.3, 87, 99; 348/341, 360; 726/26; 713/189; 380/210
See application file for complete search history.

(56) References Cited

U.S. PATENT DOCUMENTS

| | | | |
|---|---|---|---|
| 5,257,390 A | 10/1993 | Asprey | |
| 5,268,676 A | 12/1993 | Asprey et al. | |
| 5,353,409 A | 10/1994 | Asprey et al. | |
| 5,721,842 A | 2/1998 | Beasley et al. | |
| 5,732,212 A | 3/1998 | Perholtz et al. | |
| 5,884,096 A | 3/1999 | Beasley et al. | |
| 5,936,602 A * | 8/1999 | Tsuchida et al. | 345/99 |
| 5,937,176 A | 8/1999 | Beasley et al. | |
| 5,978,389 A | 11/1999 | Chen | |
| 6,112,264 A | 8/2000 | Beasley et al. | |
| 6,119,148 A | 9/2000 | Chen | |
| 6,138,191 A | 10/2000 | Fujii et al. | |
| 6,271,822 B1 * | 8/2001 | Chiang | 345/99 |
| 6,292,157 B1 * | 9/2001 | Greene et al. | 345/1.3 |
| 6,333,750 B1 | 12/2001 | Odryna et al. | |
| 6,345,323 B1 | 2/2002 | Beasley et al. | |
| 6,378,009 B1 | 4/2002 | Pinkston, II et al. | |
| 6,385,666 B1 | 5/2002 | Thornton et al. | |

(Continued)

FOREIGN PATENT DOCUMENTS

| | | |
|---|---|---|
| JP | 7160371 | 6/1995 |
| WO | 9007847 | 7/1990 |
| WO | 9811686 | 3/1998 |

OTHER PUBLICATIONS

Bloks, R.H.J., The IEEE-1394 High Speed Serial Bus, Philips J. Res., vol. 50, No. 1/2 (1996) 209-216.

(Continued)

*Primary Examiner* — Thu Ha Nguyen

(57) ABSTRACT

The present invention discloses a remote network management system for coupling a series of remote serial devices, servers, and computers to one or more user workstations allowing for selective access of the remote devices. The remote serial devices, servers, and computers are all connected to a remote management unit which interfaces the user workstations to the remote devices. The power supply of each remote device is also connected to the remote management unit through a controllable power supply. The video from the remote networking equipment is digitized and optimized by an LCD controller located within the remote management unit before it is compressed for transmission. An option menu containing a menu of all the remote devices allows a user to select and operate any of the remote devices. The option menu is also utilizes to selectively control the power to the remote serial devices, servers, and computers.

40 Claims, 13 Drawing Sheets

(56) References Cited

U.S. PATENT DOCUMENTS

| | | | |
|---|---|---|---|
| 6,388,658 B1 | 5/2002 | Ahern et al. | |
| 6,539,418 B2* | 3/2003 | Schneider et al. | 709/203 |
| 6,557,170 B1 | 4/2003 | Wilder et al. | |
| 6,600,468 B1* | 7/2003 | Kim et al. | 345/87 |
| 6,621,520 B1* | 9/2003 | Sawanobori | 348/341 |
| 6,633,905 B1 | 10/2003 | Anderson et al. | |
| 6,681,250 B1 | 1/2004 | Thomas et al. | |
| 6,701,380 B2 | 3/2004 | Schneider et al. | |
| 6,845,395 B1* | 1/2005 | Blumenau et al. | 709/223 |
| 6,886,029 B1* | 4/2005 | Pecus et al. | 709/203 |
| 7,196,644 B1* | 3/2007 | Anderson et al. | 341/118 |
| 7,508,442 B2* | 3/2009 | Watanabe et al. | 348/360 |
| 2002/0065927 A1* | 5/2002 | Janik et al. | 709/231 |
| 2002/0178279 A1* | 11/2002 | Janik et al. | 709/231 |
| 2003/0074474 A1* | 4/2003 | Roach et al. | 709/246 |
| 2003/0076438 A1* | 4/2003 | Ishimaru | 348/372 |
| 2003/0140158 A1* | 7/2003 | Lee et al. | 709/231 |
| 2004/0083266 A1* | 4/2004 | Comstock et al. | 709/204 |
| 2004/0107288 A1* | 6/2004 | Menninger et al. | 709/231 |
| 2004/0205213 A1* | 10/2004 | Paz et al. | 709/231 |
| 2005/0125519 A1* | 6/2005 | Yang et al. | 709/223 |
| 2005/0140803 A1* | 6/2005 | Ohtsuka et al. | 348/239 |
| 2005/0216949 A1* | 9/2005 | Candelora et al. | 725/134 |
| 2005/0259112 A1* | 11/2005 | Suzukawa et al. | 345/603 |
| 2005/0268236 A1* | 12/2005 | Kosaka | 715/718 |
| 2006/0031550 A1* | 2/2006 | Janik et al. | 709/231 |
| 2006/0109502 A1* | 5/2006 | Nakajima et al. | 358/1.15 |
| 2006/0137015 A1* | 6/2006 | Fahrny et al. | 726/26 |
| 2006/0250858 A1* | 11/2006 | Houda et al. | 365/189.12 |
| 2008/0037975 A1* | 2/2008 | Nakajima | 396/104 |
| 2009/0160973 A1* | 6/2009 | Houda et al. | 348/231.2 |
| 2009/0175591 A1* | 7/2009 | Gondhalekar et al. | 386/83 |
| 2011/0255690 A1* | 10/2011 | Kocher et al. | 380/210 |
| 2011/0264923 A1* | 10/2011 | Kocher et al. | 713/189 |
| 2012/0030559 A1* | 2/2012 | Manion et al. | 715/234 |
| 2012/0072488 A1* | 3/2012 | Manion et al. | 709/203 |
| 2013/0290480 A1* | 10/2013 | Manion et al. | 709/217 |

OTHER PUBLICATIONS

Luling, Reinhard, Managing Large Scale Broadband Multimedia Services on Distributed Media Servers, Multimedia Computing and Systems, IEEE International Conference on Florence Italy, Los Alamitos, CA, USA, IEEE Comput. Soc, vol. 1, Jun. 7, 1999, 320-325.

* cited by examiner

SYSTEM FOR VIDEO DIGITIZATION AND IMAGE CORRECTION FOR USE WITH A COMPUTER MANAGEMENT SYSTEM

FIELD OF THE INVENTION

The present invention relates generally to a system for video digitization and image correction. Specifically, the improved video digitization system of the present invention utilizes an LCD controller to digitize the video from a remote computer for transmission via a KVM switch to a user workstation. The LCD controller also performs the functions of video mode detection, auto-adjustment for sampling phase and frequency, picture alignment, color alignment, color adjustment, upscaling/downscaling, and image position.

BACKGROUND OF THE INVENTION

In a typical computer environment, a Local Area Network ("LAN") allows for one or more computer servers to be connected to several computers such that the resources of each server are available to each of the connected computers. The LAN is typically comprised of networking equipment such as routers, hubs, switches, etc. In such a configuration, a dedicated keyboard, video monitor and mouse may be employed for each computer and computer server.

To maintain proper operation of the LAN, the system administrator must maintain and monitor the individual networking equipment, servers, and computers. This maintenance frequently requires the system administrator to perform numerous tasks from a user console connected to the networking equipment, server, or computer. For example, to reboot a computer or to add or delete files, the system administrator is often required to operate the server or computer from its local user console, which may be located at a substantial distance from the system administrator's computer and from other computers or servers connected to the LAN. Therefore, to accomplish the task of system administration, the system administrator must often physically relocate to access the local user consoles of remotely located servers and computers. As an alternative, dedicated cables may be installed from each remotely located server and computer to the system administrator's user console to allow the system administrator to fully access and operate the remote computer equipment. However, this alternative requires substantial wiring and wire harnessing, both of which may require tremendous cost. Additionally, as the distance between the system administrator's user console and the remote computer equipment increases, a decrease in the quality of the transmitted signal often results. Thus, dedicated cables between the system administrator's user console and remote computer equipment may not be a feasible alternative.

In some situations, it is desirable to manage the networking equipment, servers, and computers located at a location remote from the system administrator. If the distance is great enough, the Internet is commonly utilized to control computers from a remote location. For example, a software program such as pcAnywhere may be utilized to access a remote computer over the Internet or a LAN utilizing the keyboard, video monitor, and cursor control device (e.g., a mouse) attached to a local user workstation. Remote computer access programs, such as pcAnywhere, typically require that host software is installed on the remote computer and client software is installed on the user workstation. To access a remote computer, a user of the user workstation selects the desired remote computer from a list and enters the appropriate username and password. Once access has been granted to the remote computer, the user utilizes the keyboard, video monitor, and cursor control device attached to the local user workstation to access and operate the remote computer.

Hardware solutions also exist for operating a remote computer from a user workstation over the Internet or via a modem. In contrast to the software solutions, the hardware solutions do not typically require host and/or client software. Instead, the hardware solutions typically utilize a keyboard, video monitor, and mouse ("KVM") switch which is accessible over the Internet or LAN via a common protocol, such as transfer control protocol/Internet protocol ("TCP/IP"). The hardware solutions may also utilize a modem to connect to the Internet or to communicate through the public telephone network. Generally, a user or system administrator access the remote computers attached to the KVM switch utilizing an Internet browser or client software associated with the KVM switch. Once the remote computer has been selected, the remote computer's video signal is routed to the user workstation's video monitor and a user may then utilize a keyboard and/or mouse to control the remote computer. The KVM switch may additionally include a connection to the power source of the remote computer for a hard reboot in case of system failure.

The aforementioned hardware and software solutions generally utilize a compression algorithm to reduce the necessary bandwidth required to transmit the video signals. For example, the remote network management system of the present invention uses the compression algorithm disclosed in application Ser. No. 10/233,299, which is incorporated herein by reference, to reduce and compress the digital data that must be transmitted to the remote computers and/or video display devices. Generally, video signals generated by a personal computer have both spatial and interframe redundancies. For example, in a near idle personal computer, the only change between successive frames of video might be the blinking of a cursor. Even as a user types a document, a majority of the screen does not change over a period of time. Hence, the compression algorithm used by the present invention takes advantage of these redundancies, both between successive frames of video and within each individual frame, to reduce the amount of digital video signal data that is transmitted. Reducing the amount of digital data transmitted over the communication medium decreases communication time and decreases the required bandwidth.

Most forms of video compression known in the art require complicated calculations. For example, Moving Pictures Experts Group ("MPEG") video compression algorithms use the discrete cosine transform. Also, the MPEG standard relies on the recognition of "motion" between frames, which requires calculation of motion vectors that describe how portions of the video image change over a period of time. Since these algorithms are calculation intensive, they either require relatively expensive hardware that performs such calculations quickly or extended transmission times that allow for slower hardware to complete the calculations.

In addition to complexity, many existing video compression techniques are lossy (i.e., they do not transmit all of the video signal information in order to reduce the required bandwidth). Typically, such lossy techniques either reduce the detail of a video image or reduce the number of colors utilized. Although reducing the number of colors could be part of an adequate compression solution for some computer management systems applications, in many other applications, such a result defeats the intended purposes of the computer management system.

A keyboard, video monitor, and mouse ("KVM") switching system may be utilized to allow one or more user workstations to select and control any one of a plurality of remote computers via a central switching unit. Such systems are well known in the art and have been used by system administrators for at least ten years.

Digital KVM switches traditionally use a circuit block called a video digitizer to convert high-speed red, green, and blue analog video signals to a digital representation. At the center of traditional circuits is a video speed A/D converter. Support circuitry surrounding this chip is complex, since the video digitizer needs to handle a variety of pixel clocks and phase shifts, and also needs to detect a blank video edge when switching between different computers or servers, which are the source of the signals.

For a quality video representation, the video digitizer depends on the detection of horizontal and vertical synchronization signals and adjusts the phase shift and pixel clock for each target video signal. This adjustment must occur regardless of the video cards and cable lengths utilized in the KVM switch system. The phase shift adjustment is critical, and if not accurate, will introduce noise into the digital representation which cannot be removed.

Prior designs of digital KVM switches use a triple A/D converter and digital data processor, or triple A/D converter and software to do different adjustments. However, the adjustment time often takes a few seconds when operators switch from one computer to another. Also, many electronic parts are needed to implement these functions.

The following references, which are discussed below, were found to relate to the field of computer management systems: Asprey U.S. Pat. No. 5,257,390 ("Asprey '390 patent"), Asprey U.S. Pat. No. 5,268,676 ("Asprey '676 patent"), Asprey U.S. Pat. No. 5,353,409 ("Asprey '409 patent), Perholtz et al. U.S. Pat. No. 5,732,212 ("Perholtz"), Chen U.S. Pat. No. 5,978,389 ("Chen '389 patent"), Chen U.S. Pat. No. 6,119,148 ("Chen '148 patent"), Fujii et al. U.S. Pat. No. 6,138,191 ("Fujii"), Odryna et al. U.S. Pat. No. 6,333,750 ("Odryna"), Beasley U.S. Pat. No. 6,345,323 ("Beasley"), Schneider et al. U.S. Pat. No. 6,539,418 ("Schneider"), and Wilder et al. U.S. Pat. No. 6,557,170 ("Wilder").

The Asprey '390 patent discloses an extended range communications link for coupling a computer to a mouse, keyboard, and/or video monitor located remotely from the computer. The end of the link that is coupled to the computer has a first signal conditioning network (i.e., a network of circuitry that dampens the ringing and reflections of the video signals and biases them to a predetermined voltage level) that conditions the keyboard, video monitor and mouse signals. Conditioning the video monitor signals includes reducing amplitude in order to minimize the amount of "crosstalk" that is induced on the conductors adjacent to the video signal conductors during transmission of the video signals. This first signal conditioning network is coupled to an extended range cable having a plurality of conductors that transmits the conditioned signals, power, and logic ground potentials to a second signal conditioning network (i.e., a network of circuitry that terminates the video signals using a voltage divider and amplifier), which restores the video signals to their original amplitude and outputs them to a video monitor.

The Asprey '676 patent discloses a communications link for use between a computer and a display unit, such as a video monitor, that allows these two components to be located up to three hundred (300) feet apart. An encoder located at the computer end of the communications link receives analog red, green, and blue signals from the computer and inputs each signal to a discrete current amplifier that modulates the signal current. Impedance matching networks then match the impedance of the red, green and blue signals to the impedance of the cable and transmit the signals to discrete emitter-follower transistors located at the video monitor end of the cable. Thereafter, these signals are amplified and then inputted to a video monitor. Concurrently, the horizontal synchronization signal is inputted to a cable conductor and its impedance is not matched to the impedance of the cable, thereby allowing the conductor to attenuate the horizontal synchronization signal and reduce noise radiation.

The Asprey '409 patent discloses an extended range communications link for transmitting transistor-transistor logic video signals from a local computer to a video monitor located up to a thousand feet (1,000) from the computer. The link includes a first signal conditioning circuit (i.e., a circuit that reduces the amplitude of the video signals, biases the signals to a selected potential, and applies them to discrete conductors of an extended cable) located at the computer end of the link for conditioning the received signals and transmitting the signals via the extended cable to a second signal conditioning circuit. The second signal conditioning circuit (i.e., a circuit that utilizes a threshold or pair of thresholds to effect reconstruction of the video signals prior to applying the signals to a video monitor) receives the transmitted video signals prior to inputting the signals to the video monitor. According to the Asprey '409 patent, performance of this process reduces the appearance of high frequency video noise on the keyboard clock conductor of the transmission cable, thereby preventing keyboard errors.

Perholtz discloses a method and apparatus for coupling a local user workstation, including a keyboard, mouse, and/or video monitor, to a remote computer. Perholtz discloses a system wherein the remote computer is selected from a menu displayed on a standard personal computer video monitor. Upon selection of a remote computer by the system user, the video signals of the remote computer are digitized and transmitted to the video monitor of the local user workstation. The video signals are digitized utilizing a video CPU capable of converting the inputted analog video signals into a digital representation. The system user may also control the remote computer utilizing the local user workstation's keyboard and monitor. The Perholtz system is also capable of bi-directionally transmitting mouse and keyboard signals between the local user workstation and the remote computer. The remote computer and the local user workstation may be connected either via the Public Switched Telephone System ("PSTN") and modems or via direct cabling.

The Chen '389 patent discloses a device for multiplexing the video output of a plurality of computers to a single video monitor. The Chen system includes three sets of switches for receiving the red, green, and blue components of the video signals from each computer. To select the video output of a specific computer for display on the video monitor, a user inputs two video selecting signals into a control signal generating circuit. Depending upon the inputted video selecting signals, the control signal generating circuit produces an output signal corresponding to the selected video output. Thereafter, a control signal is generated that indexes the three sets of switches to switch the video signals being output by the desired computer to the single video monitor. The three sets of switches transfer the incoming video signals to three sets of switch circuits and current amplifying circuits that provide input and output impedance matching, respectively. The tuned video signals are then displayed on the single video monitor.

The Chen '148 patent discloses a video signal distributor that receives, processes, and distributes video signals received from one or more computers to a plurality of video monitors. The video signal distributor includes three transistor-based, voltage-amplifying circuits to individually amplify the red, green and blue video signals received from each computer prior to transmitting these signals to a video monitor. The video signal distributor also includes a synchronization signal buffering device that receives horizontal and vertical synchronization signals from each computer and generates new synchronization signals based upon the quantity of video signals that are output to the video monitors.

Fujii discloses a system for selectively operating a plurality of computers that are connected to one common video monitor. The Fujii system includes a data input device for entering data in any one of the plurality of connected computers. The system also includes a main control circuit, which is connected to the data input device, and a selection circuit for providing the entered data and receiving the video signals from the selected computer. A user selects a remote computer by supplying the command code associated with the desired remote computer utilizing the keyboard and/or mouse. A selection circuit receives the inputted commands and identifies the selected computer. The selection circuit then sends a signal indicative of the selected remote computer to a main control circuit, which provides communication between the keyboard, video monitor, and mouse and the selected remote computer.

Similar to Perholtz, Beasley discloses a specific implementation of a computerized switching system for coupling a local keyboard, mouse and/or video monitor to one of a plurality of remote computers. In particular, a first signal conditioning unit includes an on-screen programming circuit that displays a list of connected remote computers on the local video monitor. To activate the menu, a user depresses, for example, the "print screen" key on the local keyboard. The user selects the desired computer from the list using the local keyboard and/or mouse.

According to Beasley, the on-screen programming circuit requires at least two sets of tri-state buffers, a single on-screen processor, an internal synchronization generator, a synchronization switch, a synchronization polarizer, and overlay control logic. The first set of tri-state buffers couples the red, green, and blue components of the video signals received from the remote computer to the video monitor. That is, when the first set of tri-state buffers are energized, the red, green, and blue video signals are passed from the remote computer to the local video monitor through the tri-state buffers. When the first set of tri-state buffers are not active, the video signals from the remote computer are blocked. Similarly, the second set of tri-state buffers couples the outputs of the single on-screen processor to the video monitor. When the second set of tri-state buffers is energized, the video output of the on-screen programming circuit is displayed on the local video monitor. When the second set of tri-state buffers is not active, the video output from the on-screen programming circuit is blocked. Alternatively, if both sets of tri-state buffers are energized, the remote computer video signals are combined with the video signals generated by the on-screen processor prior to display on the local video monitor.

The on-screen programming circuit disclosed in Beasley also produces its own horizontal and vertical synchronization signals. To dictate which characters are displayed on the video monitor, the CPU sends instructional data to the on-screen processor. This causes the on-screen processor to retrieve characters from an internal video RAM for display on the local video monitor.

The overlaid video image produced by the on-screen processor, a Motorola MC141543 on-screen processor, is limited to the size and quantity of colors and characters that are available with the single on-screen processor. In other words, the Beasley system is designed to produce an overlaid video that is sized for a standard size computer monitor (i.e., not a wall-size or multiple monitor type video display) and is limited to the quantity of colors and characters provided by the single on-screen processor.

During operation of the Beasley system, a remote computer is chosen from the overlaid video display. Thereafter, the first signal conditioning unit receives keyboard and mouse signals from the local keyboard and mouse and generates a data packet for transmission to a central cross point switch. The cross point switch routes the data packet to the second signal conditioning unit, which is coupled to the selected remote computer. The second signal conditioning unit then routes the keyboard and mouse command signals to the keyboard and mouse connectors of the remote computer. Similarly, video signals produced by the remote computer are routed from the remote computer through the second signal conditioning unit, the cross point switch, and the first signal conditioning unit to the local video monitor. The horizontal and vertical synchronization video signals received from the remote computer are encoded on one of the red, green or blue video signals. This encoding reduces the quantity of cables required to transmit the video signals from the remote computer to the local video monitor.

Odryna discloses a video graphics system capable of multiplexing one or more video sources to plural video display devices. The red, green, and blue components of the video signal from the video source(s) are initially converted to a digital format by three analog-to-digital converters located in a video distribution hub. The digitized video is next transmitted to a switch which transmits the digitized video to the proper remote display devices. The video distribution hub is also capable of accepting digital input from a video source.

Schneider discloses a method and system for remotely accessing and controlling a target switch or computer using a controlling computer connected to a keyboard, video monitor, and mouse. The target switch and/or computer is connected to the controlling computer via a central controller. Bi-directional keyboard and mouse signals are transmitted between the remote target switch/computer and the controlling computer. To facilitate the transmission of the bi-directional keyboard and mouse signals, the keyboard and mouse signals are digitized and serialized before transmission from the remote target switch/computer to the controlling computer and vice versa. Unidirectional video signals are also transmitted from the remote target switch/computer, through the central controller, to the controlling computer for display on a video monitor. The central controller includes a video digitizer that receives and converts the analog video signals output by the remote target switch/computer to a digital format. Schneider discloses utilizing three analog-to-digital ("A/D") converters to convert the red, green, and blue components of the video signal to a digital format. The central controller stores the converted signals in digital form in a digital memory as digital video data. After the digital video data has been properly packetized and compressed, it is transmitted to the controlling computer. The controlling computer then depacketizes, decompresses, and converts the received video signals to an analog format for display on a video monitor.

Wilder discloses a keyboard, video monitor, mouse, and power ("KVMP") switching system having an on screen display circuit that provides a visual means for accessing the KVMP switch. A first set of switching circuits coupled to a plurality of computers and the on screen display circuit allows a user to access and control any of the remote computers using a local keyboard, video monitor, and mouse. A second set of switching circuits coupled to the power supply of each remote computer and the on screen display circuit allows a user to control the electrical power to each remote computer. To select a remote computer using the Wilder system, a user activates the on-screen display by entering a hot key either with the keyboard and/or mouse. Initially, the on-screen display prompts the user to enter a username and password. Once the user has been verified, the user is provided a list of all attached remote computers. The user utilizes the local keyboard and mouse to select and control the power supply of the desired remote computer. Wilder incorporates a single on-screen processor for generation of the list of remote computers.

In view of the foregoing, a need clearly exists for an improved video digitizer capable of rapidly adjusting the video signal when a user switches from one remote computer to another. The improved video digitizer should also be capable of correcting many problems associated with video transmission in KVM switches, such as phase shift adjustments, video mode detection, etc.

SUMMARY OF THE INVENTION

The present invention provides a self-contained remote network management system for administrating a remote computer networking environment from one or more local user workstations with attached peripheral devices (i.e., keyboard, video monitor, cursor control device, etc.). The remote network management system of the present invention allows a user located at a user workstation to access, operate, and control networking equipment, servers, and computers located at a remote location. The remote network management system also allows a user to control the power supply to each piece of remote equipment. The networking equipment (e.g., hubs, switches, routers, etc.) is typically controlled via a serial interface. In contrast, servers and computers are controlled and operated utilizing a keyboard, video monitor, and mouse.

The remote networking equipment, servers, and computers are all connected to a remote management unit ("RMU"), and in turn, the RMU is connected to the Internet or a LAN via an Ethernet or modem connection. The RMU has serial ports for connection to the networking equipment as well as keyboard, video, and cursor control device ports for connection to the servers and computers. The RMU additionally contains a port for connection to a power supply capable of controlling the power to the networking equipment, servers, and computers. Standard cabling is utilized to connect the networking equipment, servers, and computers to the appropriate ports on the RMU.

To transmit digitized video from the RMU to the user workstation, the present invention utilizes improved system for video digitization and image correction. To accomplish this, the present invention replaces the A/D converter, and much of its associated circuitry, with a Liquid Crystal Display ("LCD") controller. The present invention utilizes internal functions built into the LCD controller and applies them to common KVM switch problems. For example, some of these functions include video mode detection, auto-adjustment support for sampling phase and frequency, picture alignment, color alignment, color adjustment, upscaling/downscaling, and image position. By utilizing an LCD controller, the present invention provides a more efficient and simpler method for designing and implementing KVM switches.

The RMU also provides compatibility between various operating systems and/or communication protocols, including but not limited to, those manufactured by Microsoft Corporation ("Microsoft") (Windows), Apple Computer, Inc. ("Apple") (Macintosh), Sun Microsystems, Inc. ("Sun") (Solaris), Digital Equipment Corporation ("DEC"), Compaq Computer Corporation ("Compaq") (Alpha), International Business Machines ("IBM") (RS/6000), Hewlett-Packard Company ("HP") (HP9000) and SGI (formerly Silicon Graphics, Inc.) (IRIX).

To utilize the remote network management system of the present invention, a user first initiates a management session by utilizing client software located on a user workstation to connect to the RMU. Alternatively, the user may utilize an Internet browser to connect to the RMU. The user is then prompted by the RMU to provide a user name and a password. The RMU is capable of storing multiple profiles and different levels of access for each profile. Once a user has been authenticated, the user is provided an option menu on the user workstation's monitor produced by option menu circuitry located in the RMU. The option menu consists of a menu listing all the networking equipment, servers, and computers at the remote location. The option menu additionally contains a menu allowing a user to control the power to each piece of remote equipment. The user selects the desired networking equipment, server, or computer by utilizing the keyboard and/or cursor control device attached to the user workstation. Once a user makes a selection, the user is provided access to the remote equipment as if the user is physically located at the remote site.

In one embodiment, the RMU and the user workstation communicate via TCP/IP. Before transmission via TCP/IP, the unidirectional video signals (i.e., from the RMU to the user workstation) are digitized by an LCD controller. The LCD controller captures video output from the initiating computer at a speed of at least 20 frames/second and converts the captured analog video signals to a digital representation of pixels. Each pixel is digitally represented with 5 bits for red, 5 bits for green, and 5 bits for blue. The digital representation is then stored in a raw frame buffer. The compression algorithm then processes the digital data contained in the raw frame buffer. The compression algorithm is actually a combination of four sub-algorithms (i.e., the Noise Reduction and Difference Test, Smoothing, Caching, and Bit Splicing/Compression sub-algorithms), which operate as follows:

Noise Reduction and Difference Test:

As discussed above, digitization of the analog video signals is necessary to allow these signals to be transmitted via a digital communication medium (e.g., a network, LAN, WAN, Internet, etc.). However, a detrimental side effect of the digitization process is the introduction of quantization errors and noise into the video signals. Therefore, the Noise Reduction and Difference Test sub-algorithm ("NRDT sub-algorithm") is designed to reduce the noise introduced during the digitization of the video signals. In addition, the NRDT sub-algorithm simultaneously determines the differences between the recently captured frame of video (i.e., the "current frame") and the previously captured frame of video (i.e., the "compare frame").

First, the NRDT sub-algorithm divides the current frame, which is contained in the raw frame buffer, into 64×32 blocks of pixels. Alternatively, other sizes of blocks may be used (e.g., 8×8 pixels, 16×16 pixels, 32×32 pixels, etc.) based upon criteria such as the size of the entire video frame, the bandwidth of the communication medium, desired compression yield, etc.

After the current frame is divided into blocks, a two-level threshold model is applied to the block of pixels to determine whether it has changed with respect to the compare frame. These two thresholds are the pixel threshold and the block threshold.

First, a given pixel is examined and the value of each of the three colors (i.e., red, green, and blue) of the pixel is calculated with the value of its corresponding pixel in the compare frame. From this calculation, a distance value is computed. If the distance value is greater than the pixel threshold (i.e., the first threshold of the two-level threshold), this distance value is added to a distance sum. This process is performed for each pixel in the block.

Next, after the distance value of all of the pixels in the block have been calculated and processed in the aforementioned manner, the resulting value of the distance sum is compared to the block threshold (i.e., the second threshold of the two-level threshold). If the distance sum exceeds the block threshold, then this block of pixels is considered changed in comparison to the corresponding block of pixels in the compare frame. If a change is determined, the compare frame, which is stored in the compare frame buffer, will be updated with the new block of pixels. Furthermore, the new block of pixels will be further processed and transmitted in a compressed format to the user workstation.

In contrast, if the distance sum is not greater than the block threshold, the block of pixels is determined to be unchanged. Consequently, the compare frame buffer is not updated, and this block of pixels is not transmitted to the user workstation. Eliminating the transmission of unchanged blocks of pixels reduces the overall quantity of data to be transmitted, thereby increasing transmission time and decreasing the required bandwidth.

The NRDT sub-algorithm is ideal for locating both a large change in a small quantity of pixels and a small change in a large quantity of pixels. Consequently, the NRDT sub-algorithm is more efficient and more accurate than known percentage threshold algorithms that simply count the number of changed pixels in a block of pixels. With such an algorithm, if a few pixels within the block of pixels have changed drastically (e.g., from black to white), the algorithm would consider the block of pixels to be unchanged since the total number of changed pixels would not exceed the percentage threshold value. This result will often lead to display errors in the transmission of computer video.

Consider, for example, a user that is editing a document. If the user were to change a single letter, such as changing an "E" to an "F," only a few pixels of the video image would change. However, based upon this change, the resulting document is dramatically different than the original document. A percentage threshold algorithm would not register this change and, therefore, would lead to a display error. A percentage threshold algorithm, by only looking at the number of pixels within a block that have changed, generally fails to recognize a video image change in which a few pixels have changed substantially. However, the NRDT sub-algorithm used by the present invention, by virtue of its two-level threshold, will recognize that such a block of pixels has significantly changed between successive frames of video.

Smoothing:

When the NRDT sub-algorithm determines that a block of pixels has changed, the digital data that represents this block is further processed by a smoothing sub-algorithm. This smoothing sub-algorithm reduces the roughness of the video image that is caused by the noise introduced during the analog-to-digital conversion.

First, each digital pixel representation is converted to a representation that uses a lower quantity of bits for each pixel. It is known in the art to compress color video by using a fewer number of bits to represent each color of each pixel. For example, a common video standard uses 8 bits to represent each of the red, green, and blue components of a video signal. Because such a scheme uses 24 total bits to represent a pixel, this representation is commonly referred to as "24 bit RGB representation". If only the four most significant bits of the red, green, and blue components of the pixel are used to represent its color in lieu of all eight bits, the total amount of digital data used to represent the block of pixels, and frame of video, is reduced by fifty percent.

In contradistinction, the smoothing sub-algorithm incorporates a more intelligent method of reducing the size of an RGB representation. This method uses a Color Code Table ("CCT") to map specific RGB representations to more compact RGB representations. Both the compression and decompression algorithms of the present invention use the same CCT. However, different color code tables may be chosen depending on the available bandwidth, the capabilities of the local display device, etc.

For each block of pixels, a histogram of pixel values is created and sorted by frequency such that the smoothing sub-algorithm may determine how often each pixel value occurs. Pixel values that occur less frequently are compared to pixel values that occur more frequently. To determine how similar pixel values are, a distance value is calculated based upon the color values of the red, green, and blue ("RGB") components of each pixel. During the histogram analysis, a map of RGB values to color codes (i.e., a CCT) is created. If a less frequently occurring pixel value needs to be adjusted to a similar, more frequently occurring pixel value, the CCT is used to map the less frequently occurring pixel value to the color code of the more frequently occurring pixel value. Thus, the noise is efficiently removed from each block and the number of bits used to represent each pixel is reduced.

For illustrative purposes, suppose that an 8×8 pixel block is being processed. Further suppose that of the 64 pixels in the current block, 59 are blue, 4 are red, and 1 is light blue. Further assume that a low frequency threshold of 5 and a high frequency threshold of 25 are used. In other words, if a pixel value occurs less than 5 times within a block, it is considered to have a low frequency. Similarly, if a pixel value occurs more than 25 times within a block, it is considered to have a high frequency. In the preferred embodiment of the present invention, the smoothing sub-algorithm ignores pixel values occurring between these two thresholds. Therefore, in the present example, the smoothing sub-algorithm determines that the red and light blue pixels have a low frequency, and the blue pixels have a high frequency.

In the next step, the values of the 4 red pixels and the 1 light blue pixel are compared with the value of the blue pixels. In this step, a pre-determined distance threshold is used. If the distance between the less frequent pixel value and the more frequent pixel value is within this distance threshold, then the less frequent pixel value is converted to the more frequent pixel value. Therefore, in our present example, it is likely that the light blue pixel is close enough in value to the blue pixel that its distance is less than the distance threshold. Consequently, the light blue pixel is mapped to the blue pixel. In contrast, it is likely that the distance between the red and blue pixels exceeds the distance threshold and, therefore, the red pixel is not mapped to the blue pixel. With the smoothing sub-algorithm of the present invention, although the red pixels occur rarely, the distance between the red pixel value and the blue pixel value is large enough that the red pixels are not converted to blue pixels. In this manner, the smoothing sub-algorithm of the present invention increases the redundancy in video frames by eliminating changes caused by superfluous noise introduced during the analog-to-digital conversion while retaining real changes in the video image.

Caching:

After the smoothing sub-algorithm has been applied to the digital video image data, an optional caching sub-algorithm may be applied to further minimize the bandwidth required for transmitting the video images. The caching sub-algorithm relies on a cache of previously transmitted blocks of pixels. Similar to the NRDT sub-algorithm, the caching sub-algorithm is performed on a block of pixels within the video frame. Again, any block size may be used (e.g., 8×8, 16×16, 32×32 or 64×32).

First, the caching sub-algorithm performs a cache check, which compares the current block of pixels with blocks of pixels stored in the cache. The cache may store an arbitrarily large number of previous frames. A larger cache increases the likelihood of more cache hits. However, memory and hardware requirements increase when the size of the cache is increased. Furthermore, the number of comparisons, and thus the processing power requirements, also increases when the size of the cache increases.

A "cache hit" occurs when a matching block of pixels is located within the cache. A "cache miss" occurs if a matching block of pixels is not found in the cache. When a cache hit occurs, the new block of pixels does not have to be retransmitted. Instead, a message and a cache entry identification ("ID") are sent to the remote participant equipment. Generally, this message and cache entry ID will consume less bandwidth than that required to transmit an entire block of pixels.

If a "cache miss" occurs, the new block of pixels is compressed and transmitted to the user workstation. Also, both the RMU and user workstation update their respective cache by storing the new block of pixels in the cache. Since the cache is of limited size, older data is overwritten. One skilled in the art is aware that various algorithms can be used to decide which older data should be overwritten. For example, a simple algorithm can be employed to overwrite the oldest block of pixels within the cache, wherein the oldest block is defined as the least recently transmitted block.

In order to search for a cache hit, the new block of pixels must be compared with all corresponding blocks of pixels located within the cache. There are several ways in which this may be performed. In one embodiment, a cyclic redundancy check ("CRC") is computed for the new block of pixels and all corresponding blocks of pixels. The CRC is similar to a hash code for the block. A hash code is a smaller, yet unique, representation of a larger data source. Thus, the cache check process can compare CRCs for a match instead of comparing the whole block of pixels. Specifically, a "cache hit" occurs if the CRC of the current block of pixels matches the CRC of any other blocks of pixels in cache. Because the CRC is a smaller representation of the block, less processing power and time are needed to compare CRCs. Furthermore, it is possible to construct a cache in which only the CRCs of blocks of pixels are stored at the remote participant locations. Thus, memory and processor time are saved if a comparison of CRCs is performed in lieu of a comparison of a whole blocks of pixels.

Bit Splicing/Compression:

Once the NRDT, smoothing, and optional caching sub-algorithms are performed, each block of pixels that must be transmitted is compressed preferably by using the Joint Bi-level Image Group ("JBIG") lossless compression algorithm.

The JBIG compression algorithm was designed for black and white images, such as those transmitted by facsimile machines. However, the compression algorithm utilized by the present invention can compress and transmit color video images. Therefore, when utilizing the JBIG compression algorithm, the color video image must be bit-sliced, and the resulting bit-planes must be compressed separately.

A bit plane of a color video image is created by extracting a single bit from each pixel color value in the color video image. For example, if 8 bits are used to represent the color of the pixel, then the color video image is divided into 8 bit planes. The compression algorithm works in conjunction with the CCT discussed above to transmit the bit plane containing the most significant bits first, the bit plane containing the second most significant bits second, etc. The CCT is designed such that the most significant bits of each pixel color are stored first and the lesser significant bits are stored last. Consequently, the bit planes transmitted first will always contain the most significant data, and the bit planes transmitted last will always contain the least significant data. Thus, the remote video monitor will receive video from the RMU progressively, receiving and displaying the most significant bits of the image before receiving the remaining bits. Such a method is less sensitive to changes in bandwidth and will allow a user to see the frame of video as it is transmitted, rather than waiting for all details of the frame to be sent.

Decompression:

Decompression occurs after the video signals have arrived at the user workstation. That is, at the point that decompression of the video signals is performed, the user workstation has received compressed video signals from the RMU. The user workstation operates as a decompression device by executing a decompression software algorithm. Along with any transmitted video or data signals, the RMU transmits messages to the decompression devices regarding the portions of the video that yielded cache hits. In response, the decompression device constructs the video frame based upon the transmitted video signals and the blocks of pixels contained in its local cache. Also, the decompression device updates its local cache with the new blocks of pixels received from the RMU. In this manner, the decompression device caches remain synchronized with the compression device cache. Both the compression device and the decompression device update their respective cache by replacing older video data with newer video data.

Furthermore, the video signals transmitted by the RMU have been compressed using a lossless compression algorithm as discussed above. Therefore, the decompression device must reverse this lossless compression. This is done by identifying the changed portions of the video image, based upon flags transmitted by the RMU. From this flag information, the decompression software reconstructs full frames of video.

In addition, the decompression process converts the video frame to its original color scheme by reversing the CCT conversion. Therefore, the decompression software, like the RMU, locally stores a copy of the same CCT used to compress the video data. The CCT is then used to convert the video data received from the RMU to a standard RGB format that may be displayed on the monitor attached to the user workstation.

The decompression algorithm can be implemented in the remote network management system of the present invention in a variety of embodiments. For example, in one embodiment, it can be implemented as a software application that is executed by the user workstation. In an alternate embodiment, the decompression algorithm can be implemented to execute within a web browser such as Internet Explorer or Netscape® Navigator®. Such an embodiment eliminates the need for installation of application specific software on the user workstation. Also, this embodiment allows the RMU to easily transmit the video signals to any user workstation with Internet capabilities, regardless of the distance at which the computer is located from the initiating computer. This feature reduces the cabling cost associated with the remote network management system of the present invention.

Security:

Since the present invention can be used to display video signals at locations that may be at a great distance from the RMU, it is important to ensure that the video signal transmission is secure. If the transmission is not secure, hackers, competitors, or other unauthorized users could potentially view confidential information contained within the video signals. Therefore, the remote network management system of the present invention is designed to easily integrate with digital encryption techniques known in the art. In one embodiment of the present invention, a 128-bit encryption technique is used both to verify the identity of the RMU and to encrypt and decrypt the transmitted video and data signals. In this embodiment, a 128-bit public key RSA encryption technique is used to verify the remote participant, and a 128-bit RC4 private key encryption is used to encrypt and decrypt the transmitted signals.

Finally, since remote network management system of the present invention allows for platform independent communications, the compression algorithm utilized by the preferred embodiment of the present invention does not use operating system specific hooks, nor does it employ platform specific GDI calls.

In the preferred embodiment of the present invention, the compression algorithm described above is used to transmit the video signals. However, the video transmission system of the present invention is not limited to such an embodiment. Rather, this system may be employed with any compression algorithm without departing from the spirit of the present invention.

Therefore, it is an object of the present invention to provide an improved computer management system which utilizes an LCD controller to provide enhanced video digitization.

Further, it is an object of the present invention to provide an improved computer management system which utilizes an LCD controller to provide enhanced video mode detection, auto-adjustment support for sampling phase and frequency, picture alignment, color alignment, color adjustment, upscaling, downscaling, and image position.

It is an object of the present invention to provide an improved, remote network management system that enables a user to control a remote networking environment from one or more local user workstations.

Further, it is an object of the present invention to provide a remote network management system that allows one or more local user workstations to access and operate remote networking equipment, servers, and computers connected to a remote management unit.

It is still a further object of the present invention to provide a modular computer management system that is easy to install and operate.

In addition, it is an object of the present invention to provide a remote network management system that is relatively small in size.

Furthermore, it is an object of the present invention to provide a remote network management system that allows high resolution video to be displayed at an extended distance from the computer or server at which the video signals originate.

Further, it is an object of present invention to provide a remote network management system, which allows error-free communications between peripheral devices of a local user workstation and networking equipment, servers, and computers located at an extended distance from the local user workstation.

It is also an object of the present invention to provide a remote network management system capable of controlling the power supply to remotely located networking equipment, servers, and computers.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which.

DETAILED DESCRIPTION OF THE PREFERRED EMBODIMENTS

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention. The following presents a detailed description of the preferred embodiment (as well as some alternative embodiments) of the present invention.

Figure 1:
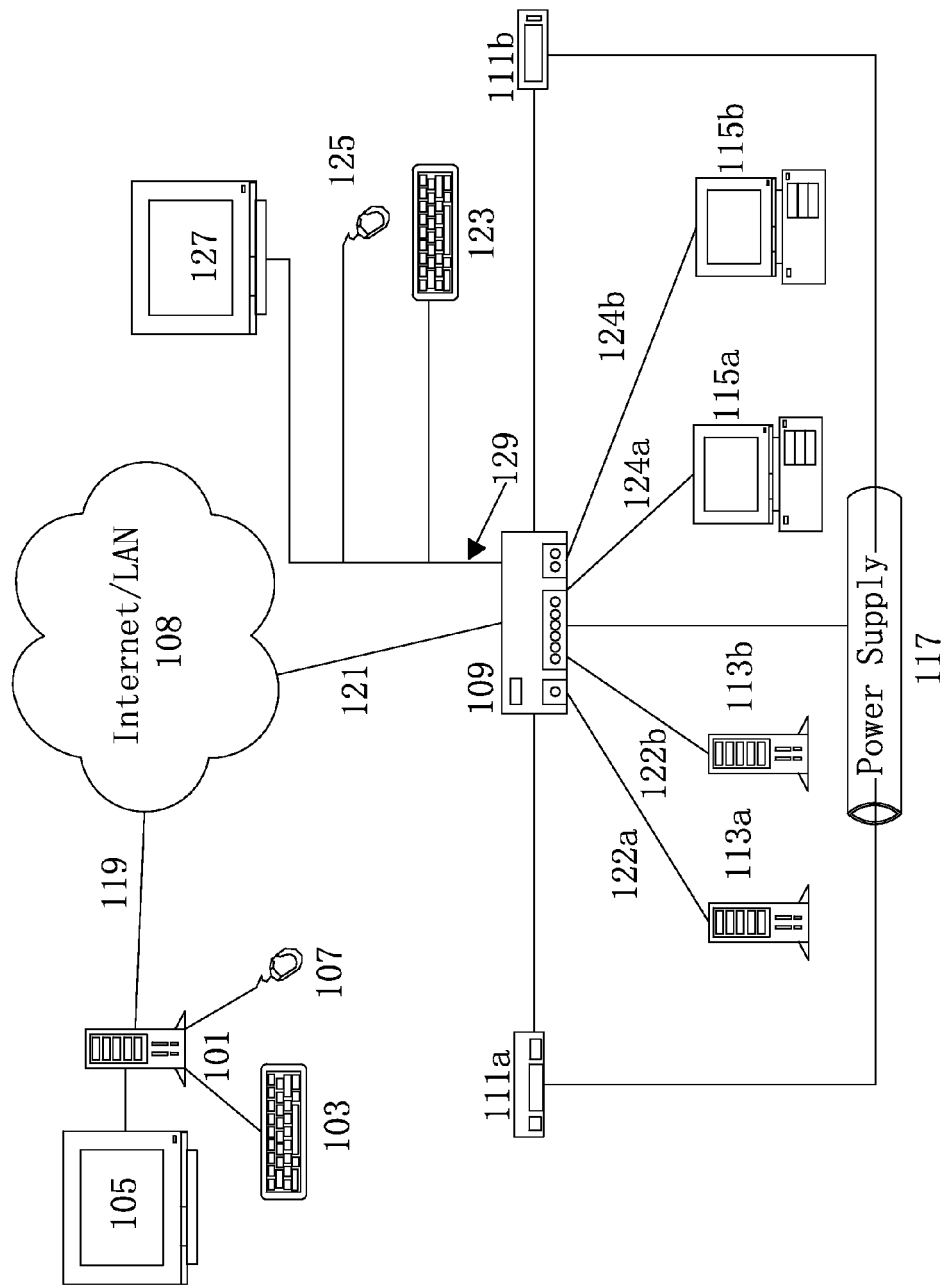
FIG. 1 is a schematic representation of a remote network management system according to the preferred embodiment of the invention illustrating the connection of a user workstation that includes a keyboard, video monitor, and cursor control device to networking equipment, servers, and computers through a remote management unit ("RMU").

Referring first to FIG. 1, depicted is the architecture of the preferred embodiment of a remote network management system in accordance with the present invention. Specifically, a remote network management system is shown including user workstation 101 having attached keyboard 103, video monitors 105, and cursor control devices 107, remote management unit ("RMU") 109, Internet/LAN 108, serial devices 111a and 111b, servers 113a and 113b, computers 115a and 115b, and power supply 117. Preferably, user workstation 101 and RMU 109 are connected to Internet/LAN 108 via cables 119 and 121, respectively; servers 113a and 113b are connected to RMU 109 by cables 122a and 122b, respectively; and computers 115a and 115b are connected to RMU 109 by cables 124a and 124b, respectively. Although CAT 5 cabling is the preferred cabling for cables 119 and 121, other cabling may be used, such as coaxial, fiber optic or multiple CAT 5 cables. CAT 5 cabling is preferred because it reduces cabling cost while maintaining the strength of signals that are transmitted over an extended distance.

Cables 119 and 121 are connected to user workstation 101 and RMU 109 by plugging each end into a RJ-45 socket located on the respective pieces of equipment to be coupled by the CAT 5 cable. Although RJ-45 sockets and plugs are preferred, other types of connector may be used, including but not limited to RJ-11, RG-58, RG-59, British Naval Connector ("BNC"), and ST connectors.

The remote management system includes local user workstation 101, preferably comprising dedicated peripheral devices such as keyboard 103, video monitor 105 and/or cursor control device 107. Other peripheral devices may also be located at workstation 101, such as printers, scanners, video camera biometric scanning devices, microphones, etc. Each peripheral device is directly or indirectly connected to user workstation 101, which is attached to Internet/LAN 109 via cable 119. Of course, wireless peripheral devices may also be used with this system. During operation, all electronic signals (i.e., keyboard signals and cursor control device signals) received at user workstation 101 from attached peripheral devices are transmitted to Internet/LAN 108 via cable 119. Thereafter, the signals are transmitted to RMU 109 via cable 121. RMU transmits the received signals to the respective remote equipment, which, in this figure, includes serial devices 111a and 111b, servers 113a and 113b, computers 115a and 115b, and power supply 117.

RMU 109 is compatible with all commonly used, present day computer operating systems and protocols, including, but not limited to, those manufactured by Microsoft (Windows), Apple (Macintosh), Sun (Unix), DEC, Compaq (Alpha), IBM (RS/6000), HP (HP9000) and SGI. Additionally, local devices may communicate with remote computers via a variety of protocols including Universal Serial Bus ("USB"), American Standard Code for Information Interchange ("ASCII") and Recommend Standard-232 ("RS-232").

To connect to the remote networking environment for administration and access, a user first initiates a remote management session utilizing user workstation 101. The user starts client software located on user workstation 101 which prompts the user for a user name and password. However, the system of the present invention may utilize any combination of identification data to authenticate a user. The user utilizes the attached keyboard 103 and/or cursor control device 107 to enter the user name and password. Once the user name and password have been entered, user workstation 101 connects to Internet/LAN 108 via cable 119. User workstation 101 may connect to Internet/LAN 108 in a variety of ways. For example, user workstation 101 may be connected to Internet/LAN 108 through an Ethernet connection. In this example, cable 119 would be a CAT 5 cable. Alternatively, user workstation 101 may connect to Internet/LAN 108 via a modem connection. In this alternative example, cable 119 would be a CAT 3 cable. The connection to Internet/LAN 108 may also be accomplished through a wireless connection which precludes the need for cable 119.

The username and password are then routed through Internet/LAN 108 to RMU 109 via cable 121. RMU 109 is connected to Internet/LAN 108 in a manner similar to user workstation 101 (i.e., through an Ethernet connection, a modem connection, or a wireless connection). RMU 109 receives the username and password and authenticates the user located at user workstation 101. Once the user has been authenticated by RMU 109, an option menu circuit located in RMU 109 provides an option menu to user 101 via monitor 105 listing all the devices accessible through RMU 109. The user makes selections from this option menu utilizing keyboard 103 and/or cursor control device 105 attached to user workstation 101. Preferably, the option menu consists of a menu in which the attached devices are arranged by their connection to RMU 109. For example, serial devices 111a and 111b preferably would be listed in a menu different from servers 113a and 113b and computers 115a and 115b. The option menu also consists of a sub-menu for controlling power supply 117.

RMU 109 may additionally contain an attached keyboard 123, cursor control device 125, and video monitor 127 which allow a user to control the attached serial devices 111a and 111b, servers 113a and 113b, and computers 115a and 115b. Keyboard 123, cursor control device 125, and video monitor 127 are connected to RMU 109 via interface cable 129. Alternatively, keyboard 123, cursor control device 125, and video monitor 127 may be connected to RMU 109 via standard keyboard, cursor control device, and video monitor connectors.

Figure 2:
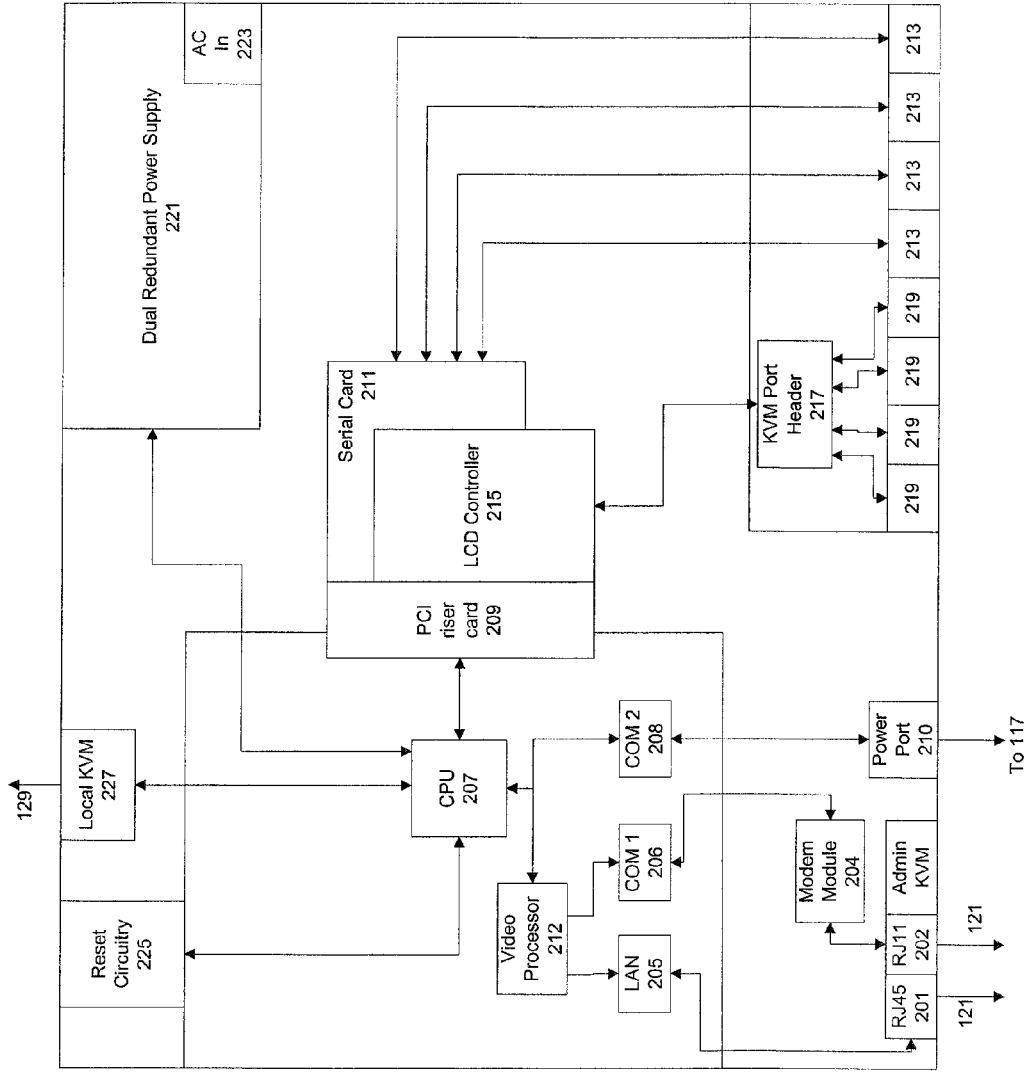
FIG. 2 is a schematic representation of the RMU shown in FIG. 1 according to the preferred embodiment of the present invention illustrating a block diagram of the internal structure of the RMU and connectors for serial devices, keyboards, video monitors, cursor control devices, and a power supply.

Referring next to FIG. 2, depicted is the preferred embodiment of RMU 109 according to the present invention. Keyboard and mouse signals arrive at RJ-45 port 201 from Internet/LAN 108 via cable 121. RMU 109 consists of RJ-45 port 201, RJ-11 port 202, Ethernet connector 205, modem module 204, communications port connector 206, CPU 207, communications port connector 208, PCI riser card 209, serial card 211, video processor 212, serial ports 213, LCD controller 215, KVM port header 217, KVM ports 219, power supply 221, power port 223, reset circuitry 225, and local KVM port 227. As shown, the keyboard and/or cursor control device signals initially arrive at RJ-45 port 201 if RMU 109 is connected to Internet/LAN 108 via an Ethernet connection. The signals are then transmitted to Ethernet connector 205 which depacketizes the signals. Alternatively, the signals may arrive from Internet/LAN 108 at RJ-11 port 202 if the keyboard and/or cursor control device signals were transmitted via a modem. In this case, the signals are transmitted to modem module 204, which demodulates the received signal, and subsequently to communications port connector 206 which depacketizes the signals.

From Ethernet connector 205 or communications port connector 206, the keyboard and/or cursor control device signals are then transmitted to CPU 207 via video processor 212. CPU 207 utilizes routing information contained within the keyboard and/or cursor control device signals to determine the proper destination for the keyboard and cursor control device signals. If the keyboard and cursor control device signals specify a command to power supply 117, CPU 207 interprets the received command (e.g., utilizing a look-up table) and sends the proper command to power supply 117 via communications port connector 208 and power port 210. Preferably, power port 210 is an RJ-45 connector to allow the RMU to interface with a power strip and control it as if it were a serial device.

Figure 2A:
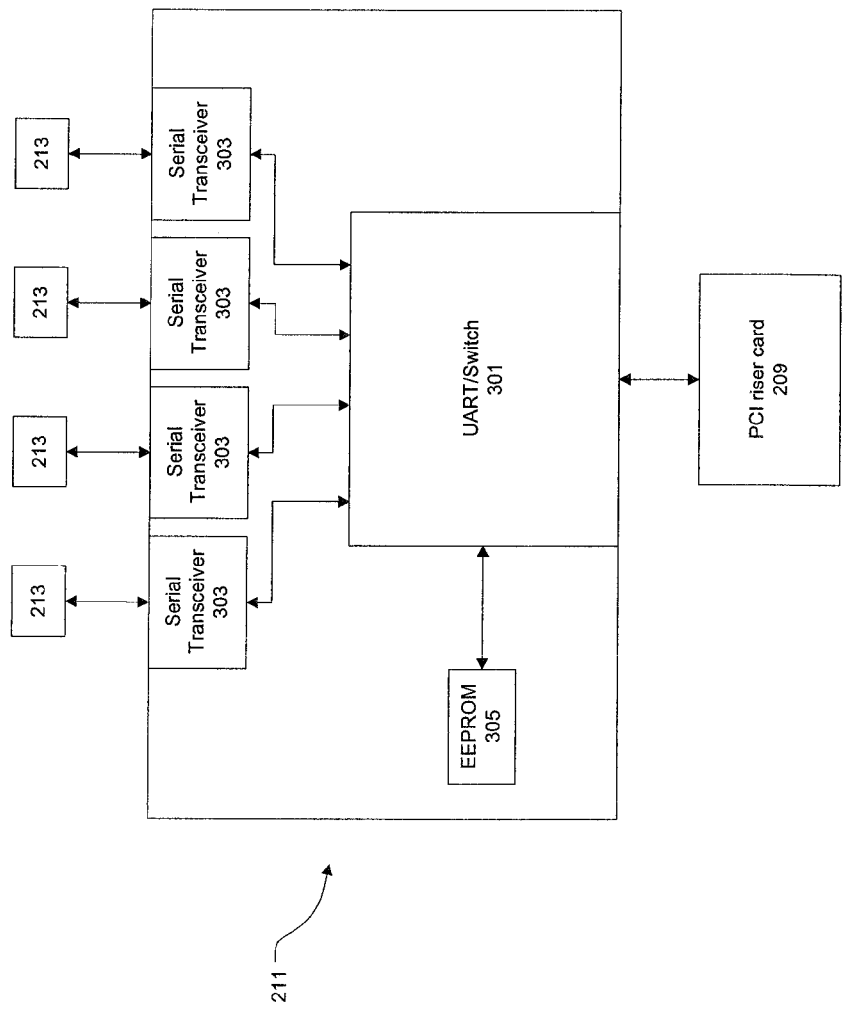
FIG. 2A is a schematic representation of the serial card shown in FIG. 2.

If CPU 207 determines that the keyboard and cursor control device signals contain a serial device routing instruction, the keyboard and cursor control device signals are transmitted to serial card 211 through PCI riser card 209. As shown in FIG. 2A, serial port 211 consists of UART/switch 301, serial transceivers 303, and programmable memory 305. Serial card 211 is capable of bi-directional signal transmission. When keyboard and/or cursor control device signals are being transmitted from PCI riser card 209 to serial port 213, the signals are initially transmitted to UART/switch 301 which determines the proper serial transceiver 303 to which the keyboard and/or cursor control device signals are to be sent. In the preferred embodiment of serial card 211, UART/switch 301 is an EXAR XR17c158. Subsequently, the analog signals are transmitted to the appropriate serial transceiver 303 which converts the signals from a parallel format to a serial format. Serial transceiver 303 is preferably a HIN23E serial transceiver from Intersil. The keyboard and/or cursor control device signals are then transmitted to serial port 213.

In contrast, when commands from serial device 111a or 111b are transmitted to CPU 207 via serial port 213, serial card 211, and PCI riser card 209, the commands are initially transmitted to serial transceiver 303 which converts the serial commands to a parallel format. Subsequently, the commands are transmitted to UART/switch 301 which re-transmits the commands to CPU 207 via PCI riser card 209. CPU 207 interprets the received commands and emulates a virtual terminal for display on video monitor 105. The present invention may incorporate any number of serial ports 213. In the example shown, two serial devices, 111a and 111b, are connected to serial ports 213a and 213b, respectively.

Figure 2B:
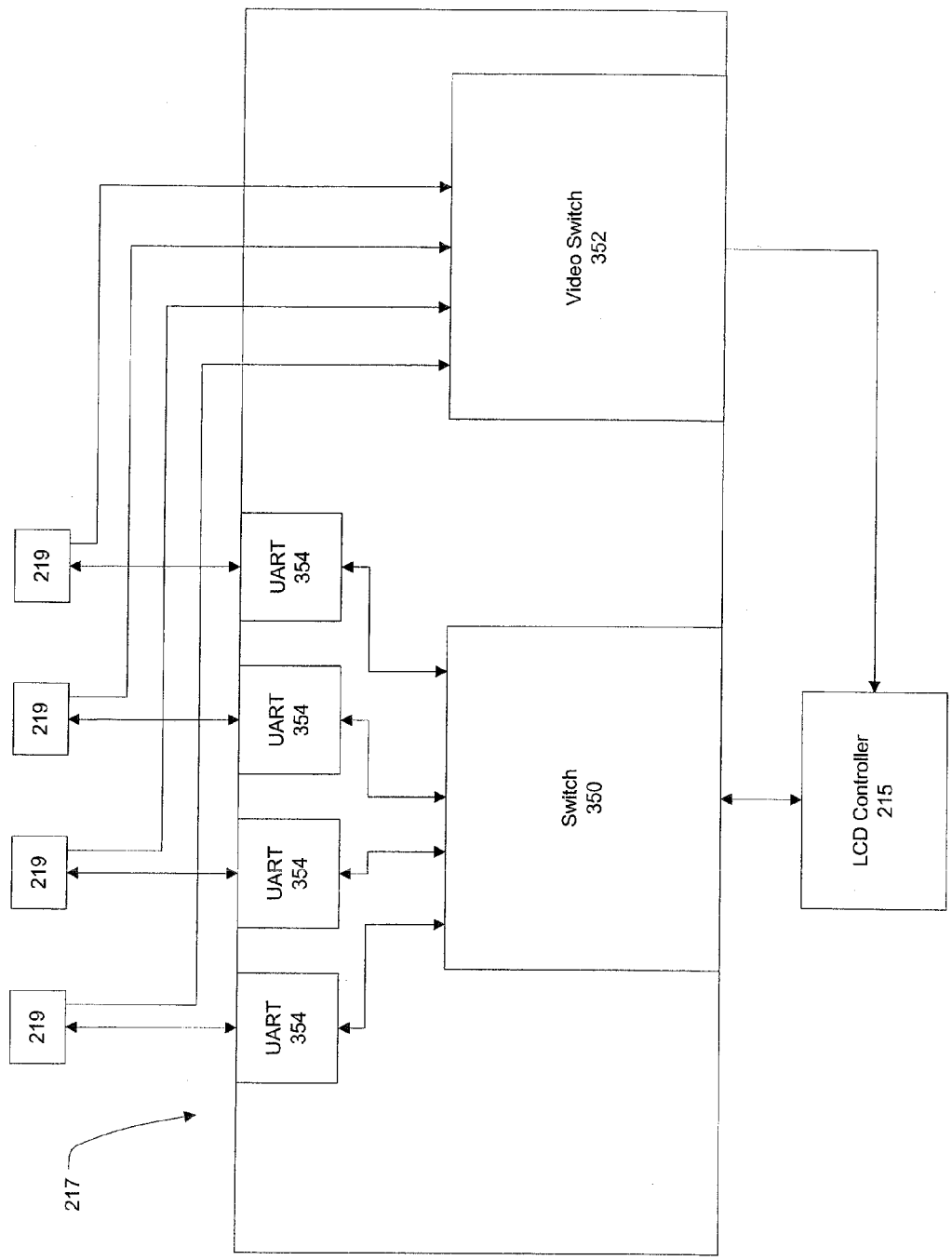
FIG. 2B is a schematic representation of the KVM port header shown in FIG. 2.

If CPU 207 determines that the keyboard and/or cursor control device signals are meant for servers 113a and 113b or computers 115a and 115b, CPU 207 transmits the keyboard and cursor control device signals through PCI riser card 209 and LCD controller 215 to KVM port header 217 which transmits the signals to the appropriate KVM port 219. As shown in FIG. 2B, KVM port header 217 consists of switch 350, video switch 352, and UARTs 354. When keyboard and/or cursor control device signals are transmitted from KVM port 219 to KVM port header 217, the signals are initially received at UART 354. UART 354 converts the received serial keyboard and/or cursor control device signals to a parallel format. The converted keyboard and/or cursor control device signals are then transmitted to switch 350 which retransmits the signals to LCD controller 215.

In a similar manner, bi-directional keyboard and/or cursor control device signals are also transmitted from LCD controller 215 to KVM port 219. Keyboard and/or cursor control device signals received from LCD controller 215 are transmitted to switch 350 located in KVM port header 217. Utilizing control signals contained within the keyboard and/or cursor control device signals, switch 350 transmits the received keyboard and/or cursor control device signals to the appropriate UART 354. UART 354 then converts the keyboard and/or cursor control device signals from a parallel format to a serial format for transmission to KVM port 219.

Figure 2C:
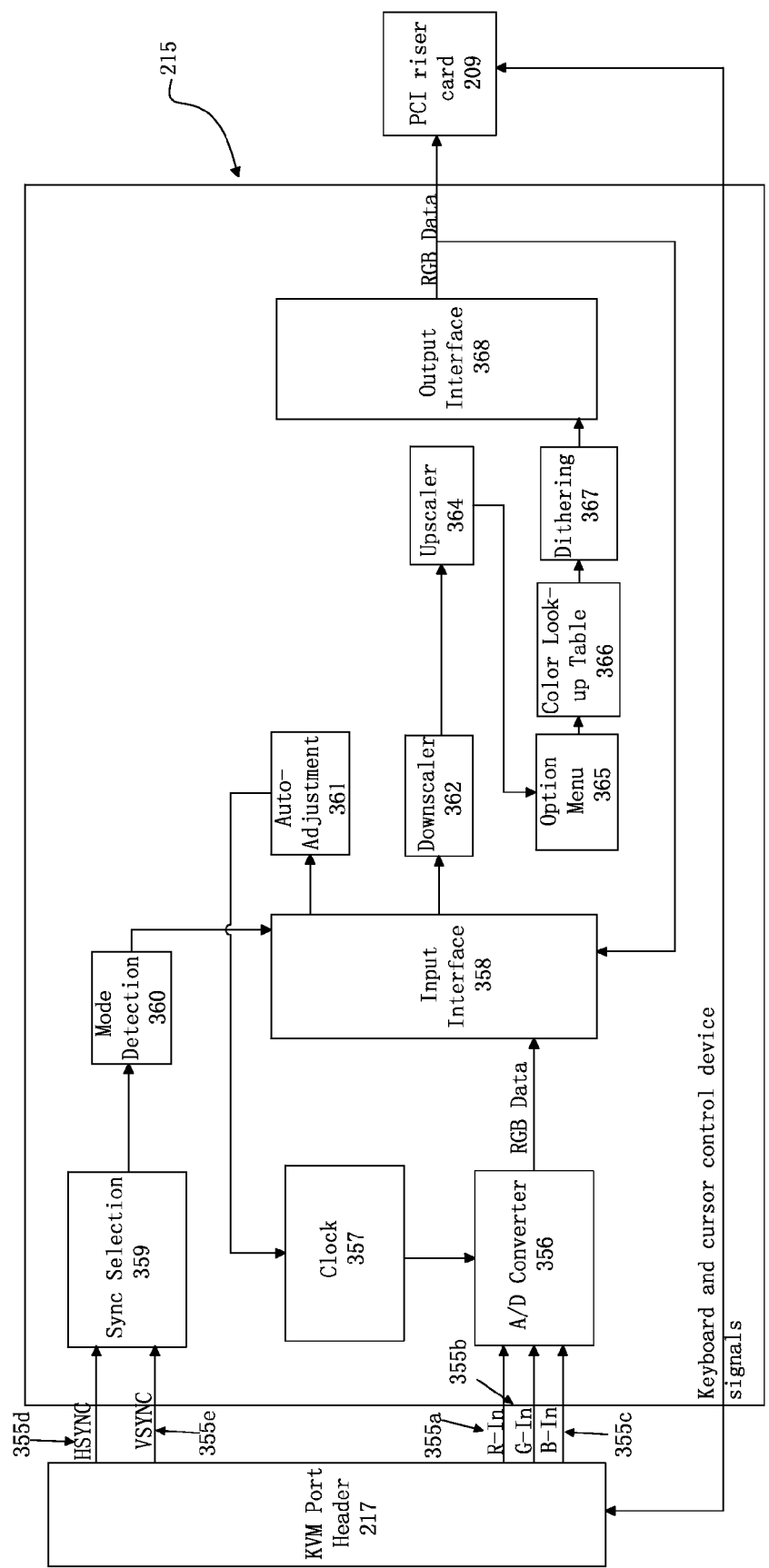
FIG. 2C is a schematic representation of the LCD controller shown in FIG. 2.

KVM port header 217 also transmits unidirectional video signals received at KVM port 219 to LCD controller 215. The analog video signals received from KVM port 219 initially are transmitted to video switch 352. Video switch 352 then retransmits the video signals to LCD controller 215 which converts the received analog video signals to a digital format. As shown in FIG. 2C, LCD controller 215 comprises R-In 355a, G-In 355b, B-In 355c, H-In 355d, V-In 355e, analog to digital ("A/D") converter 356, clock 357, input interface 358, synchronization selector 359, mode detection circuit 360, auto-adjustment circuit 361, downscaler circuit 362, upscaler circuit 364, option menu circuit 365, color lookup table 366, dithering circuit 367, and output interface 368. All keyboard and cursor control device signals transmitted from KVM port header 217 to PCI riser card 209 pass through LCD controller 215 unprocessed. In a similar manner, all keyboard and cursor control device signals transmitted from PCI riser card 209 to KVM port header 217 also pass through LCD controller 215 unprocessed.

The unidirectional video signals from KVM port header 217 arrive at LCD controller via R-In 355a, G-In 355b, B-In 355c which input the red, green, and blue components of the video signal, respectively, to LCD controller 215. Similarly, H-In 355d and V-In 355e input the horizontal synchronization signal and vertical synchronization signal, respectively, to LCD controller 215. The analog red, green, and blue components of the video signal are initially converted to a digital format by A/D converter 356 which is driven by clock 357. Once the video has been digitized, it is transmitted to input interface 358. Input interface 358 utilizes the received digital video signal to detect which color palette is being utilized by the video source.

Alternatively, the received signals may be from a digital source, in which case no A/D conversion is necessary. In such a scenario, the signals bypass A/D converter 356 and are transmitted directly to input interface 358 to detect which color palette is being utilized by the video source.

Concurrently, the horizontal and vertical synchronization signals are received at synchronization selector 359 through H-In 355d and V-In 355e. Mode detection circuit 360 utilizes the received horizontal and vertical synchronization signals to detect the frequency of the horizontal and vertical synchronization signals. Once the frequencies have been determined, the information is passed to input interface 358.

Input interface 358 utilizes the received horizontal and vertical synchronization signal frequency information in combination with the color palette information to determine the video mode of the video source. Once the video mode has been determined, the digitized video is analyzed by auto-adjustment circuit 361. Auto-adjustment circuit 361 is capable of active area detection, a brightest and lowest pixel search, pixel measurement, and phase distortion measurement. For example, auto-adjustment circuit 361 may perform a phase distortion measurement on the video signal. A phase distortion may occur if the red, green, and blue components of the video signal are not synchronized. If auto-tuning circuit 361 determines that a phase distortion exists, it updates the timing of clock 357 to compensate for the different phases of the different components of the video signal.

Once the video signal has been processed by auto-adjustment circuit 361, the video signal is transmitted to downscaler circuit 362. Downscaler circuit 362 is utilized to reduce a high resolution video signal to a lower resolution. Both the horizontal and vertical downscaling can be adjusted independently. For example, suppose the video source outputs a video signal that is 1024×768 pixels. Also suppose that the destination for the video can only accommodate a video source with a maximum resolution of 800×600 pixels. In this example, downscaler circuit 362 may be utilized to reduce the 1024×768 video source resolution to a resolution of 800×600.

However, if downscaling is not required (e.g., if the destination video accommodates higher resolutions than the source), the video signal is transmitted to upscaler circuit 364 which may be utilized to enlarge the incoming video signal. The magnification can be programmed individually for horizontal and vertical scaling. Preferably, the implemented upscaling algorithm uses interpolation with pixel enhancement, based on a free programmable transition function.

Once the video signal has been processed by downscaler circuit 362 or upscaler circuit 364, the video signal is transmitted to option menu circuit 365. Option menu circuit 365 provides the option menu to a user of the present invention. As previously discussed, the option menu contains menus for selecting a serial device, a remote server or computer, or options to control the power to all devices connected to power supply 117.

After option menu circuit 365, the video signal next enters color look-up table 366 which performs gamma correction and color component brightness and contrast adjustment on the video signal. The red, green, and blue components of the video signal are processed by three independent tables located within color look-up table 366.

The video signal next enters dithering circuit 367 which improves the visual quality of the video signal through dithering. This is achieved through temporal variation of the physically possible color values. To reduce artifacts of the temporal variation, neighboring pixels follow different sequences of variation. Alternatively, the dithering can be applied randomly as is well known in the art.

After the video signal has been properly processed by downscaler circuit 362, upscaling circuit 364, option menu circuit 365, color look-up table 366, and dithering circuit 367, the video signal is output to PCI riser card 209 by output interface 368. Optionally, output interface 368 may be utilized to adjust the timing of the video signal transmitted to PCI riser card 209.

Figure 2D:
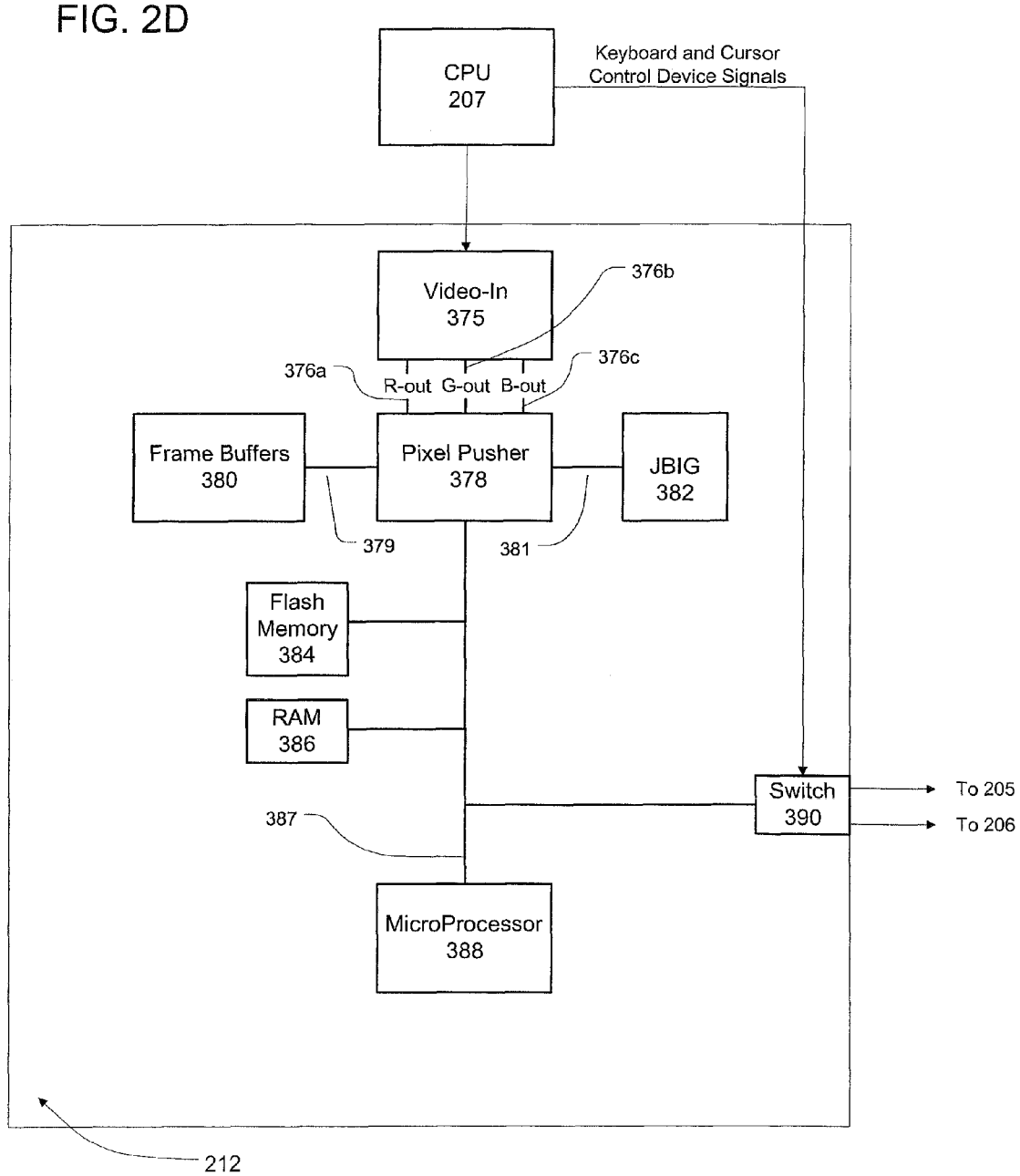
FIG. 2D is a schematic representation of the video processor shown in FIG. 2.

After the video signals have been digitized and processed by LCD controller 215, the digitized video signals are transmitted to video processor 212 via CPU 207 and PCI riser card 209. As shown in FIG. 2D, video processor 212 consists of video-in port 375, R-out 376a, G-out 376b, B-out 376c, pixel pusher 378, frame buffers 380, compression device 382, flash memory 384, RAM 386, microprocessor 388, and switch 390. Shown at the top of FIG. 2D, video-in port 375 receives the digitized video signals from CPU 207. The outputs of video-in port 375 are shown as R-out 376a, G-out 376b, and B-out 376c, which represent the red component, green component, and blue component of the digitized video signal, respectively. Video-in port 375 outputs these digitized video signal components in the form of pixels, which are transmitted to and stored in pixel pusher 378. Pixel pusher 378, flash memory 384, and Random Access Memory ("RAM") 386 communicate with microprocessor 388 via communication bus 387. Pixel pusher 378 also communicates with frame buffers 380 (e.g., raw frame buffer, compare frame buffer, etc.) and compression device 382 via communication buses 379 and 381, respectively. The compression algorithm is executed by microprocessor 388. After compression of the video signals is complete, the resulting video signals are transmitted to either Ethernet connector 205 or communications port connector 206 via switch 390.

RMU 109 also contains a power supply 221 which provides power to RMU 109. Preferably, power supply 221 is a redundant power supply which contains backup circuitry in case the main circuitry fails. Power supply 221 receives power through power port 223 from an external power source. The power to RMU is controlled by reset circuitry 225 which is interfaced directly to CPU 207. Reset circuitry 225 is utilized to turn the power on or off and to reset RMU 109.

RMU 109 also contains local KVM port 227 interfaced to CPU 207. Local KVM port 227 allows for connection of local keyboard 123, video monitor 127, and cursor control device 125 to RMU 227 via cable 129 (FIG. 1). Local keyboard 123, video monitor 127, and cursor control device 125 may be utilized for onsite control of the attached serial devices 111a and 111b, servers 113a and 113b, computers 115a and 115b, and power supply 117.

To utilize the system of the present invention, a user first initiates a remote management session at user workstation 101 and enters the required username and password. However, any unique combination of authentication information may be utilized. User workstation 101 packetizes the entered information and routes it to Internet/LAN 108 via cable 119 and then to RMU 109 via cable 121. The entered data is received at CPU 207 via RJ-45 connector 201 (or alternatively RJ-11 connector 202). Ethernet connector 205 removes the network protocol and transmits the received keyboard and/or cursor control device signals to CPU 207. CPU 207 utilizes a lookup table containing all user profiles stored in the system to authenticate the user. Different user profiles may be given different levels of access to the system. For example, certain users may only be able to access and operate computers 115a and 115b and be restricted from operating servers 113a and 113b, serial devices 111a and 111b, and power supply 117.

Once a user has been authenticated, option menu circuit 365 produces an option menu containing all the devices attached to RMU 109. In this case, the attached devices include serial devices 111a and 111b, servers 113a and 113b, computers 115a and 115b, and power supply 117. However, it would be apparent to one skilled in the art that RMU 109 may accommodate any number of serial devices, servers, computers, and associated power supplies. The option menu produced by option menu circuit 365 is compressed by video processor 212 and packetized by Ethernet connector 205 and then transmitted to user workstation 101 through RJ-45 connector RJ-45 connector 201, cable 121, Internet/LAN 108, and cable 119, in that order. The option menu is depacketized and decompressed at user workstation 101 for display on video monitor 105. The user then utilizes keyboard 103 and cursor control device 107 to select the desired device from the option menu. The user-entered keyboard and cursor control device signals are then encoded by user workstation 101, transmitted to RMU 109 via Internet/LAN 108, and subsequently decoded by CPU 207 located in RMU 109. CPU 207 interprets the received keyboard and cursor control device signals and interfaces the user with the selected device as previously described.

If the user selects to be interfaced with servers 113*a* or 113*b* or computers 115*a* and 115*b*, the video signal of the selected device is displayed on video monitor 105. The video signal initially arrives from the selected device at KVM port 219 and is routed to KVM port header 217. The video signal is then routed to LCD controller 215 which converts the analog video signal to a digital signal. The resulting digitized video signal is then routed to CPU 207 through PCI riser card 209. CPU 207 then determines the correct location to transmit the video signal (i.e., to local KVM port 227 or video processor 212). If the video signal is routed to local KVM port 129, the video signal is displayed on local video monitor 127. Alternatively, if the video signal is routed to video processor 212, it is compressed by video processor 212 and packetized by either Ethernet connector 205 or communications port connector 206 for transmission via cable 121 through either RJ-45 port 201 or RJ-11 port 202. Ethernet connector 205 or communications port connector 206 also appends any other signals (i.e., keyboard signals, cursor control device signals, etc.) onto the compressed video signal for transmission to user workstation 101.

To switch to another connected device, the user presses a "hotkey" such as "printscreen" or "F1" on keyboard 103 attached to user workstation 101 (FIG. 1). This causes option menu circuit 365 to display an option menu allowing the user to select a new serial device, server, computer, or modify the power supply to one of the connected devices.

Figure 3:
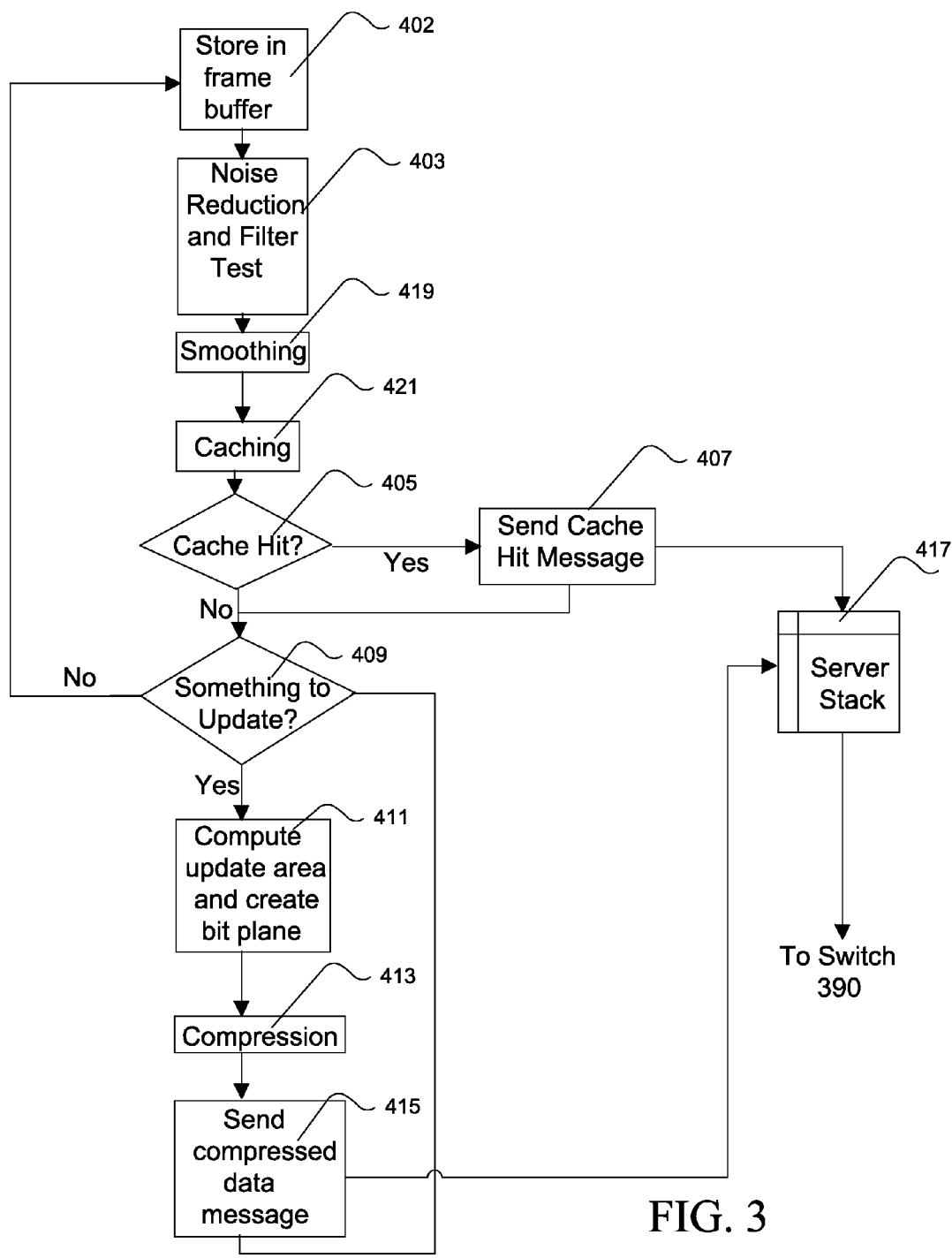
FIG. 3 depicts a flowchart of the compression algorithm utilized by the preferred embodiment of the present invention.

Referring now to FIG. 3, depicted is a flowchart illustrating the operation of the compression algorithm utilized by video processor 212 in the preferred embodiment of the present invention. The compression algorithm is executed internal to RMU 109 by video processor 212 (FIG. 2). The digitized video signal is initially stored in a raw frame buffer (step 402), which is one of the frame buffers 380 (FIG. 2D). At this point, the compression algorithm is performed to process the captured video data contained in the raw frame buffer and prepare it for transmission to user workstation 101.

The first step of the compression algorithm is the NRDT (step 403). The NRDT sub-algorithm is also executed internal to RMU 109 by video processor 212 (FIG. 2). The NRDT sub-algorithm determines which, if any, blocks of pixels have changed between the current frame and the compare frame, also discussed above.

In the preferred embodiment of the present invention, the video frame is first divided into 64×32 pixel blocks. Subsequently, the NRDT sub-algorithm is applied to each block of pixels independently. Alternative embodiments of the present invention may utilize smaller or larger blocks depending on criteria such as desired video resolution, available bandwidth, etc.

Next, the NRDT sub-algorithm employs a two-threshold model to determine whether differences exist between a block of pixels in the current frame and the corresponding block of pixels in the compare frame. These two thresholds are the pixel threshold and the block threshold.

First, each pixel of the pixel block is examined to determine if that pixel has changed relative to the corresponding pixel of the corresponding block in the compare frame. The distance value of each of the three colors (i.e., red, green, and blue) of each pixel in relation to the corresponding compare pixel is calculated, as described in greater detail below with respect to FIG. 6. If the distance value is larger than the pixel threshold (i.e., the first threshold of the two-threshold model), this distance value is added to a distance sum value.

Then, after all pixels within the pixel block have been examined, if the resulting distance sum value is greater than the block threshold (i.e., the second threshold of the two-threshold model), the block is determined to have changed. Every block of pixels in the video frame undergoes the same process. Therefore, after this process has been applied to an entire video frame, the process will have identified all pixel blocks that the process has determined have changed since the previous video frame. At this point, the compare frame is updated with the changed pixel blocks. However, the pixel blocks of the compare frame that correspond to unchanged pixel blocks of the current frame will remain unchanged. In this manner, the two-threshold model used by the NRDT sub-algorithm eliminates pixel value changes that are introduced by noise created during the analog to digital conversion and also captures the real changes in the video frame.

After the video data is processed by the NRDT sub-algorithm, it is next processed by the smoothing sub-algorithm (step 419). The smoothing sub-algorithm used by the present invention is designed to create a smooth, higher-quality video image by reducing the roughness of the video image caused by noise introduced during the analog to digital conversion.

The smoothing sub-algorithm first converts the pixel representation that resulted from the NRDT sub-algorithm into a pixel representation that uses a lesser quantity of bits to represent each pixel. This is performed using a CCT that is specially organized to minimize the size of the pixel representation. The smoothing sub-algorithm uses the CCT to choose color codes with the least number of 1-bits for the most commonly used colors. For example, white and black are assumed to be very common colors. Thus, white is always assigned 0 and black is always assigned 1. That is, white will be represented by a bit value of 0 on all planes. Black, the next most common color, will show up as a bit value of 1 on all but one plane. This reduces the quantity of data to be compressed by the compression algorithm. Then, for each pixel in the block, a color code is assigned. Simultaneously, a histogram of color codes is created to store the number of occurrences of each of the unique colors in the block of pixels. This histogram of color codes is then sorted to produce a list of color codes from the least number of occurrences to the dominant number of occurrences.

Once the sorted list of color codes is created, the next step is to merge colors. Working from the beginning of the sorted list, the smoothing sub-algorithm compares the least frequently occurring colors to the more frequently occurring colors. If the less frequently occurring color is very similar to a more frequently occurring color, then the pixels having the less frequently occurring color will be changed to the more frequently occurring color. Determination of whether two colors are similar is performed by calculating the distance between the three-dimensional points of the RGB space. The formula is:

$$\text{Distance} = \text{square root}((\text{square}(red1-red2)) + \text{square}(green1-green2) + \text{square}(blue1-blue2))$$

If the distance is within a distance threshold, the two colors are determined to be similar. In the preferred embodiment of the present invention, system performance is increased by squaring the distance threshold and comparing this value with the sum of the squares of the RGB differences. This step eliminates taking the square root of the sum, which requires a greater amount of processing time.

Each block of pixels is filtered for noise and translated from a RGB representation to a color code representation. The noise that is introduced by LCD controller 215 (FIG. 2) during conversion of the analog signals to digital signals distorts the values of some pixels. Thus, the smoothing sub-algorithm corrects distorted pixels. The smoothing sub-algorithm minimizes noise by reducing the number of different colors present in each video image block. Such smoothing creates an image with greater redundancy, thus yielding higher compression ratios.

After smoothing, caching is performed (step 421). Caching is a sub-algorithm of the overall compression algorithm executed by video processor 212 of RMU 109 (FIG. 2). Caching requires RMU 109 (FIG. 2) to retain a cache of recently transmitted images. Such a cache can be implemented and stored in RAM 386 (FIG. 2D). The caching sub-algorithm compares the most recent block of pixels with the corresponding block of pixels in the video images stored in the cache (step 405). If the most recently transmitted block of pixels is the same as one of the corresponding blocks of pixels stored in the cache, the caching sub-algorithm does not retransmit this portion of the video image. Instead, a "cache hit" message is sent to user workstation 101 that indicates that the most recently transmitted block is already stored in the cache (step 407). The "cache hit" message contains information regarding which cache contains the corresponding block of pixels, thereby allowing user workstation 101 to retrieve the block of pixels from its cache and use it do create the video image to be displayed on its attached video display device.

The next step in the process, step 409, checks to see if the NRDT determined that the block of pixels has changed since the corresponding block of pixels in the compare frame. This step can also be implemented before or in parallel with step 405. Also, steps 421, 405, and 407 may be eliminated entirely.

The main purpose of step 409 is to check if the block has changed since the last frame. If the block has not changed, there is no need to send an updated block to user workstation 101. Otherwise, if the block of pixels has changed, it is prepared for compression (step 411). In the preferred embodiment, step 409 uses a different technique than step 405. With two ways of checking for redundancy, higher compression can result. Both steps 409 and 411 are executed by a caching sub-algorithm executed by microprocessor 388 of video processor 212 (FIG. 2D).

For any areas of the image that have changed, the cache is updated, and the data is compressed before being sent to the server stack. In the preferred embodiment, the image is compressed using the IBM JBIG compression algorithm. JBIG is designed to compress black and white images. However, the present invention is designed to transmit color video images. Therefore, bit planes of the image are extracted (step 411), and each bit plane is compressed separately (step 413). Finally, the compressed image is transmitted to server stack 417 (step 415), which transmits the data to switch 390 (FIG. 2D).

Figure 4A:
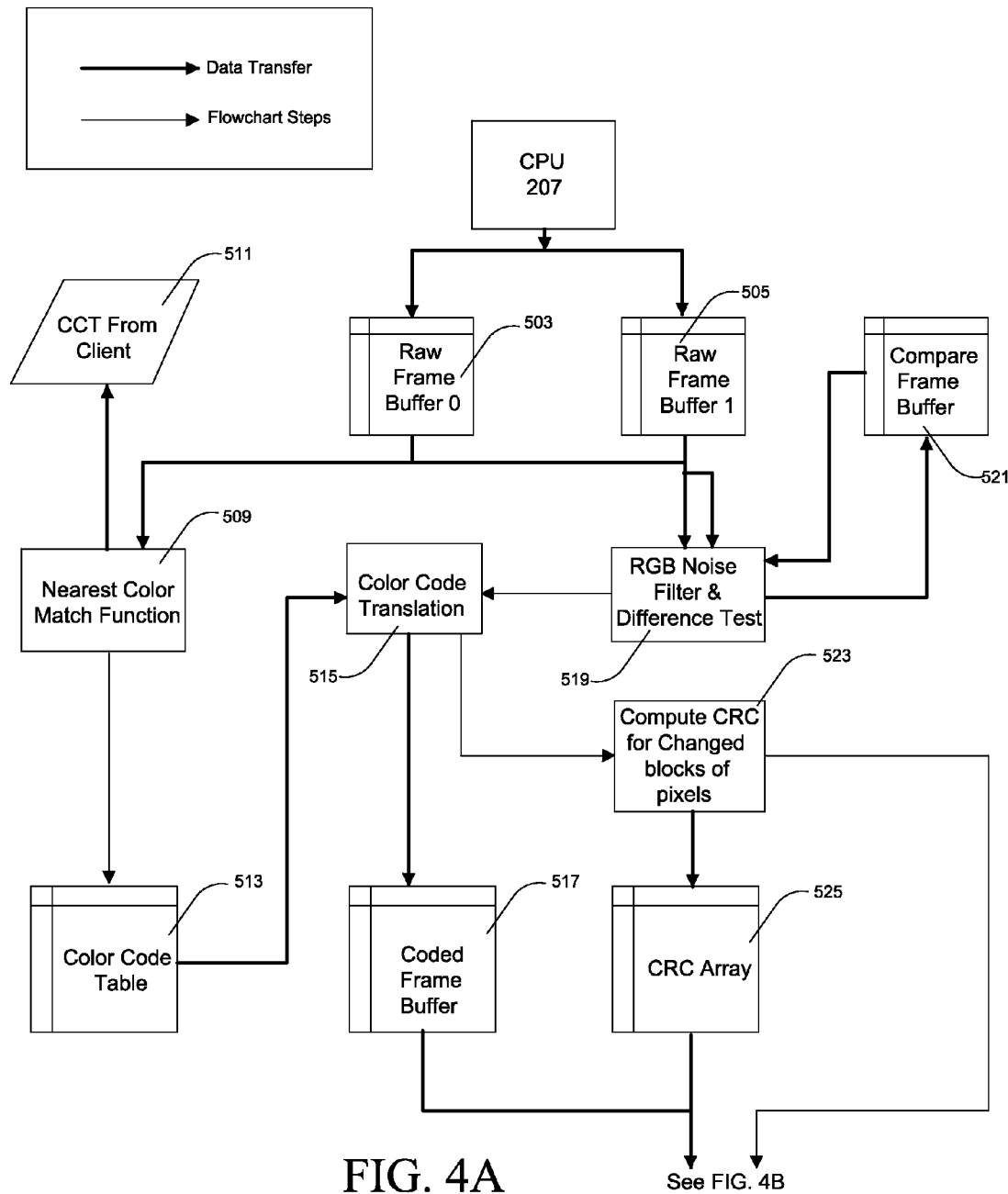
FIG. 4A depicts a flowchart that details the NRDT and smoothing sub-algorithms of the compression algorithm utilized by the preferred embodiment of the present invention.
Figure 4B:
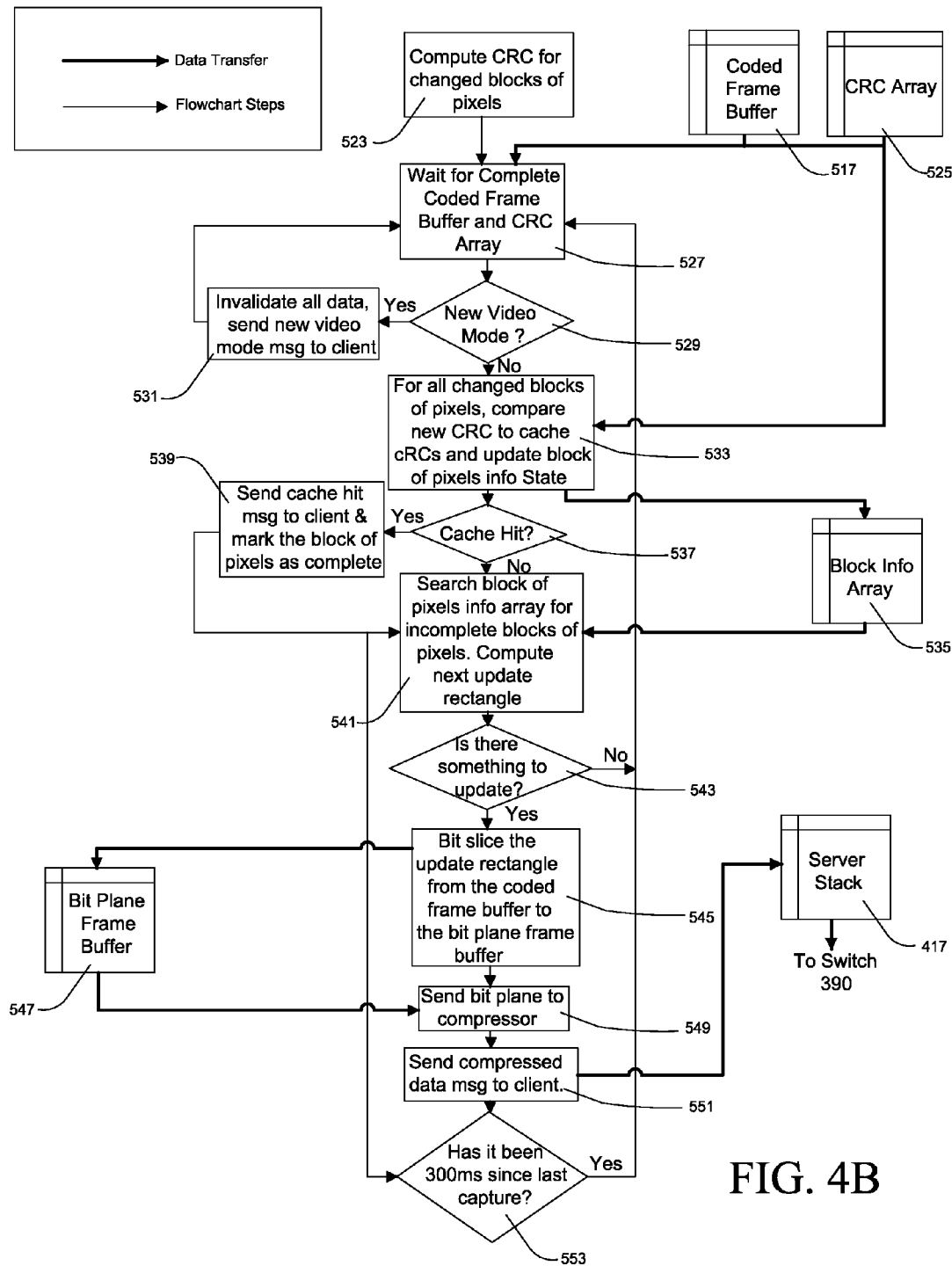
FIG. 4B depicts a flowchart that details the caching and bit splicing/compression sub-algorithms of the compression algorithm utilized by the preferred embodiment of the present invention.

FIG. 4A and FIG. 4B provide detailed flowcharts of a preferred embodiment of the compression process. The digital representation of the captured video image is transferred and stored in either frame buffer 0 503 or frame buffer 1 505. A frame buffer is an area of memory that is capable of storing one frame of video. The use of two frame buffers allows faster capture of image data. The captured frames of video are stored in frame buffer 0 503 and frame buffer 1 505 in an alternating manner. This allows the next frame of video to be captured while compression is being performed on the previous frame of video. In video processor 212, frame buffer 0 503 and frame buffer 1 505 comprise a portion of frame buffers 380 (FIG. 2D).

An NRDT test is performed on each block of pixels stored in raw frame buffer 0 503 and raw frame buffer 1 505 (step 519), which compares each block of the captured video image to the corresponding block of the previously captured video image. Step 519 compares blocks of pixels from the video image stored in the current raw frame buffer (i.e., raw frame buffer 0 503 or raw frame buffer 1 505) with the corresponding block of pixels stored in compare frame buffer 521. This step is discussed in greater detail below with respect to FIGS. 6A and 6B.

If step 519 determines that the current block of pixels has changed, then nearest color match function processes the video images contained in raw frame buffer 0 503 and raw frame buffer 1 505 (step 509) in conjunction with the information contained in the client color code table ("CCT from client") 511, which is stored in flash memory 239 (FIG. 2). The nearest color match function can be executed as software by microprocessor 388. A detailed explanation of the nearest color match function is provided below with respect to FIG. 5.

The resulting CCT 513 from the nearest color match function is used for color code translation (step 515), which translates the digital RGB representation of each pixel of the changed block of pixels to reduce the amount of digital data required to represent the video data. Color code translation receives blocks of pixels that the NRDT sub-algorithm (step 519) has determined have changed relative to the previous captured video image. Color code translation then translates this digital data into a more compact form and stores the result in coded frame buffer 517. Coded frame buffer 517 can be implemented as a portion of RAM 386 (FIG. 2D).

Alternatively, steps 509 and 515 may be performed in parallel with step 519. Performing these steps in parallel reduces the overall processing time required for each block of pixels that as changed. In this scenario, steps 509 and 515 are performed in anticipation of the block of pixels having changed. If this is the case, the processing for steps 509 and 515 may be complete as the processing for step 519 completes. Therefore, the algorithm may move directly to step 523 from step 509 without having to wait for the processing of steps 509 and 515. Otherwise, if step 519 determines that the block of pixels has not changed, and therefore the results of steps 509 and 515 are not required, these results may simply be discarded.

Upon completion of step 515, caching begins by performing a cyclical redundancy check (CRC)(step 523). Cyclic redundancy check (CRC) is a method known in the art for producing a checksum or hash code of a particular block of data. The CRCs can be computed for two blocks of data and then compared. If the CRCs match, the blocks are the same. Thus, CRCs are commonly used to check for errors. In the present invention, the CRC is used to compare a block of pixels with blocks of pixels stored in a cache. Thus, in step 523, the CRC is computed for each block of pixels that was determined to have changed by the NRDT sub-algorithm. The array of CRCs is stored in CRC array 525.

Turning next to FIG. 4B, depicted is an overview of the caching and bit splicing/compression sub-algorithms. This portion of the algorithm begins with a wait for information from coded frame buffer 517 and CRC array 525 (step 527). Next, a decision is made as to whether a new video mode has been declared (step 529). A new video mode can be declared if, for example, user workstation 101 has different bandwidth or color requirements. If a new video mode has been declared, all data is invalidated (step 531) and the sub-algorithm returns to step 527 to wait for new information from coded frame buffer 517 and CRC array 525. Downscaler circuit 362 and/or upscaler circuit 364, located in LCD controller 215, may be utilized to adjust the outputted digitized video to be compatible with the new video mode. Steps 527, 529, and 531 are all steps of the overall compression algorithm that is executed by microprocessor 388 (FIG. 2D).

If in step 529 it is deemed that a new video mode has not been declared, then the comparison of the current block of pixel's CRC with the cached CRCs is performed (step 533). This block compares the CRC data of the current video frame, which is contained in CRC array 525, with the cache of previous CRCs contained in block info array 535. Block info array 535 stores the cache of pixel blocks and the CRCs of the pixel blocks and can be implemented as a device in RAM 386 (FIG. 2D). Step 533 is also a part of the overall compression algorithm executed by microprocessor 388 (FIG. 2D).

Next, if the current block of pixels is located within the pixel block cache contained in block info array 535 (step 537), a cache hit message is sent to user workstation 101 and the block of pixels is marked as complete, or processed (step 539). Since user workstation 101 contains the same pixel block cache as RMU 109 (FIG. 2D), the cache hit message simply directs user workstation 101 to use a specific block of pixels contained in its cache to create the portion of the video image that corresponds to the processed block of pixels.

Next, a check is performed for unprocessed blocks of pixels (step 541). All blocks of pixels that need to be processed, or updated, are combined to create a compute next update rectangle. If there is nothing to update (if the video has not changed between frames), then the algorithm returns to step 527 (step 543). Thus the current frame will not be sent to the remote participation equipment. By eliminating the retransmission of a current frame of video, the sub-algorithm reduces the bandwidth required for transmitting the video.

If however, there are areas of the image that need to be updated, the update rectangle is first compressed. Thus, the update rectangle must be bit sliced (step 545). A bit plane of the update rectangle is constructed by taking the same bit from each pixel of the update rectangle. Thus, if the update rectangle includes 8-bit pixels, it can be deconstructed into 8 bit planes. The resulting bit planes are stored in bit plane buffer 547. Again, steps 541, 543, and 545 are all part of the bit splicing/compression sub-algorithm executed by microprocessor 388 of RMU 109 (FIG. 2).

Each bit plane is compressed separately by the compression sub-algorithm (step 549). In this case, compression is performed on each bit plane and the resulting data is sent to server stack 417 (step 551). In the preferred embodiment of the present invention, compression is performed by video compression device 382 (FIG. 2) (step 549). Thereafter, the compressed bit planes are sent to switch 390 (FIG. 2D).

Since the preferred embodiment captures frames 20 times a second, it is necessary to wait 300 ms between video frame captures. Thus, the algorithm waits until 300 ms have passed since the previous frame capture before returning the sub-algorithm to step 527 (step 553).

Figure 5:
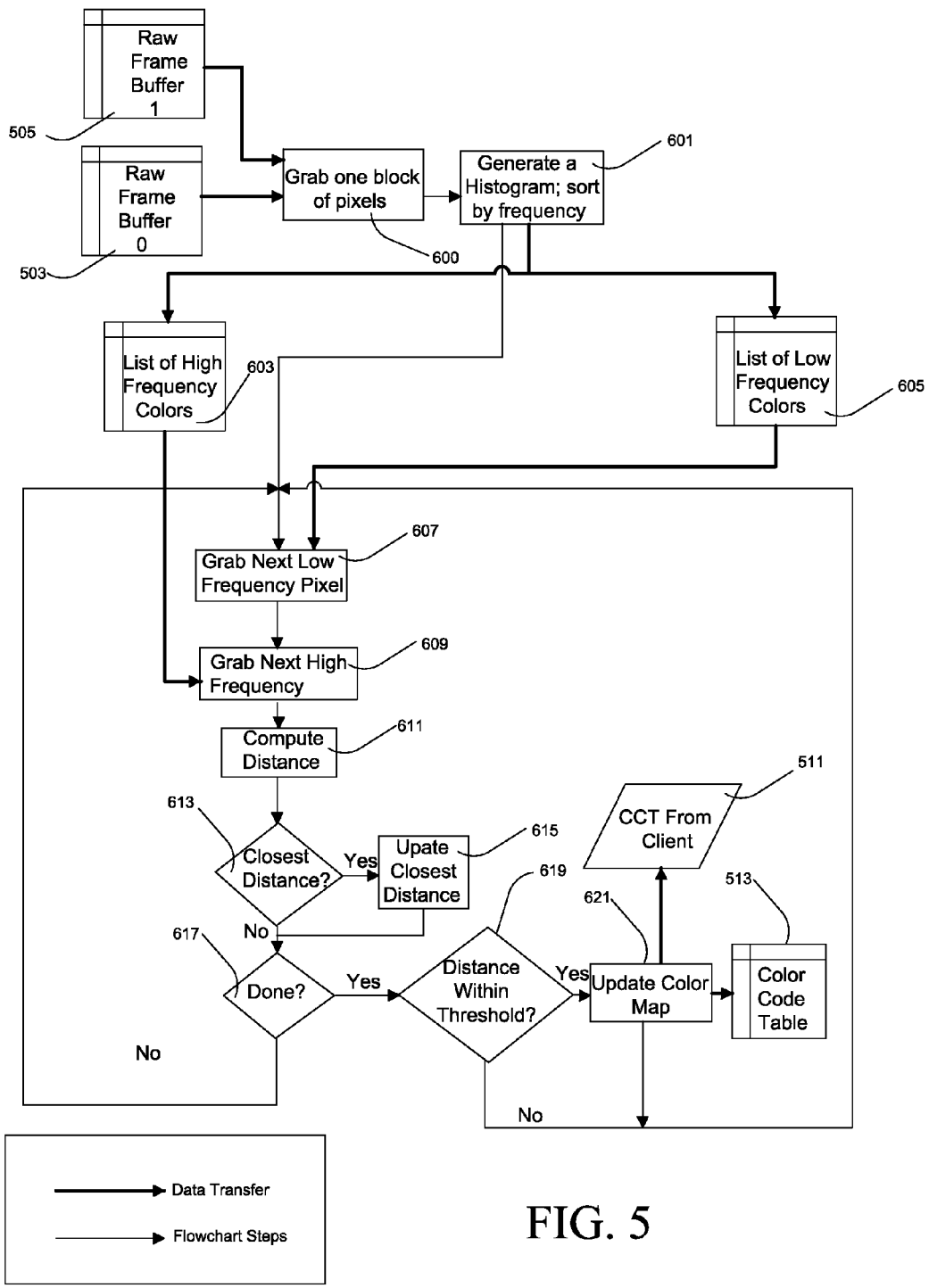
FIG. 5 depicts a flowchart that details the nearest match function and its integration with the CCT of the compression algorithm utilized by the preferred embodiment of the present invention.

Referring now to FIG. 5, illustrated is the nearest color match function (step 509) (FIG. 4A) that selectively maps less frequently occurring colors to more frequently occurring colors using a CCT. Nearest color match function processes each block of pixels in a video image successively. As seen in FIG. 5, a block of pixels is extracted from the video image stored in raw frame buffer 0 503 or raw frame buffer 1 505 (step 600). In the preferred embodiment of the present invention, the extracted block has a size of 64 by 32 pixels. However, the nearest color match function can process blocks having any size.

The nearest color match eliminates noise introduced by the A/D conversion. This is accomplished by converting less frequently occurring pixel values to similar, more frequently occurring pixel values. This is done primarily via histogram analysis and difference calculations. The nearest color match function generates a histogram of pixel values (step 601). The histogram measures the frequency of each pixel value in the block of pixels extracted during step 600. The histogram is sorted, such that a list of frequently occurring colors, popular color list 603, and a list of least frequently occurring colors, rare color list 605, are generated. The threshold for each list is adjustable.

The nearest color match function analyzes each low frequently occurring pixel to determine if the pixel should be mapped to a value that occurs often. First, a pixel value is chosen from rare color list 605 (step 607). Then, a pixel value is chosen from popular color list 603 (step 609). These distance between these two values is then computed (step 611). In this process, distance is a metric computed by comparing the separate red, green and blue values of the two pixels. The distance value, "D," can be computed in a variety of ways. One such example is:

$$D=(R2-R1)^2+(G2-G1)^2+(B2-B1)^2$$

In this formula, R1 is the red value of the low frequency pixel, R2 is the red value of the high frequency pixel, G1 is the green value of the low frequency pixel, G2 is the green value of the high frequency pixel, B1 is the blue value of the low frequency pixel, and B2 is the blue value of the high frequency pixel.

This formula yields a distance value, D, which indicates the magnitude of the similarity or difference of the colors of two pixels, such as a less frequently occurring pixel versus a more frequently occurring pixel. The goal of the sub-algorithm is to find a more frequently occurring pixel having a color that yields the lowest distance value when compared to the color of a less frequently occurring pixel. Therefore, a comparison is for each computed distance value (step 613). Every time a distance value is computed that is less than all previous distance values, the distance value is written to the closest distance variable (step 615).

Once it is determined that all more frequently occurring pixels have been compared to less frequently occurring pixels (step 617), a computation is performed to determine if the lowest occurring D is within a predefined threshold (step 619). If this D is within the threshold, CCT 513 is updated by mapping the low frequently occurring pixel to the color code value of the high frequently occurring pixel that yielded this D value (step 621). This process is repeated for all low frequency pixels and CCT 513 is updated accordingly.

Figure 6:
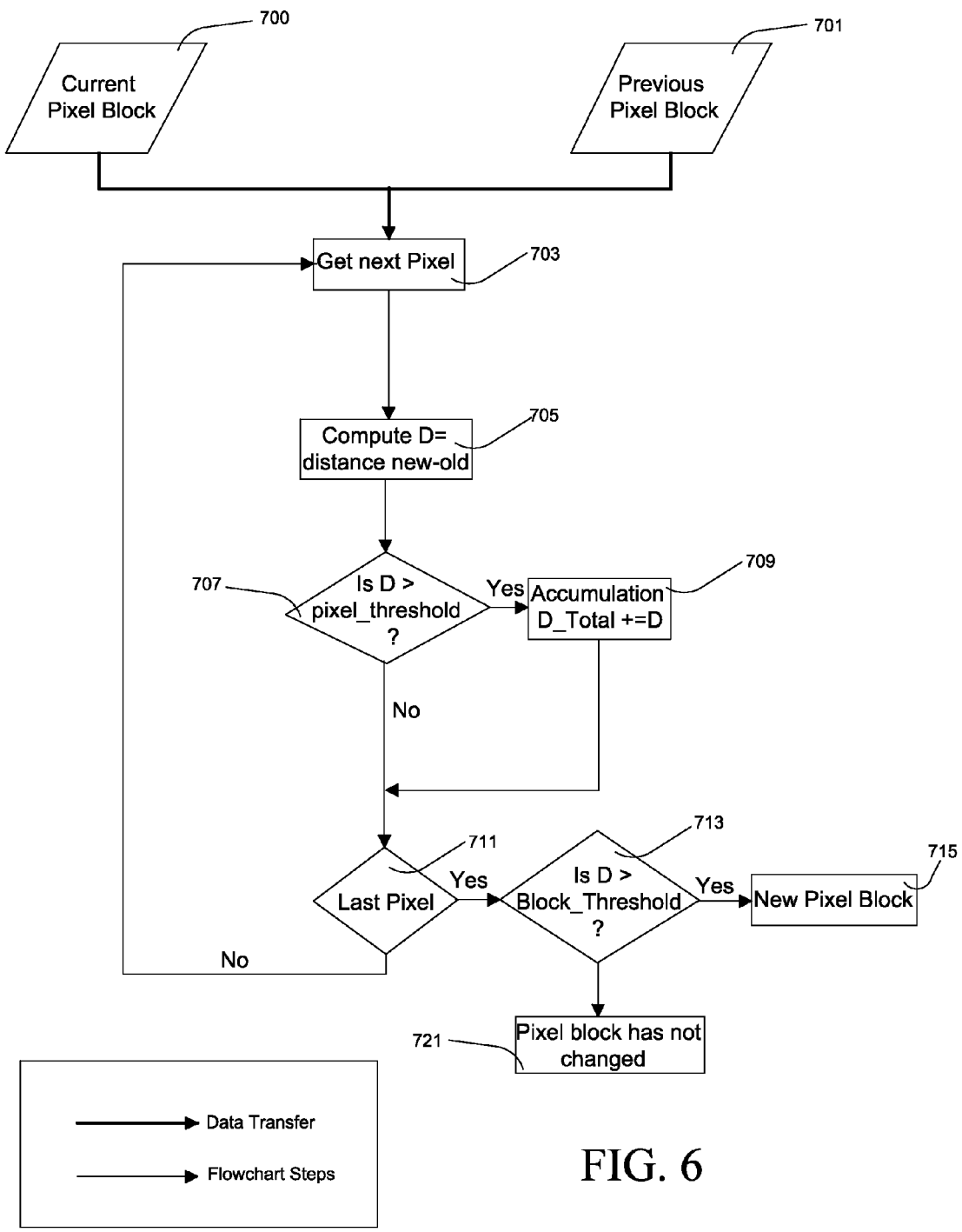
FIG. 6 depicts a flowchart that details the NRDT sub-algorithm of the compression algorithm utilized by the preferred embodiment of the present invention.

Turning to FIG. 6, step 519 (FIG. 4A) is illustrated in further detail. This process operates on every block of pixels in the video image. Current pixel block 700 represents a block of pixels of the video image contained in the current raw frame buffer (i.e., raw frame buffer 0 503 or raw frame buffer 1 505 (FIG. 4A)). Previous pixel block 701 contains the corresponding block of pixels of the video image contained in compare frame buffer 521 (FIG. 4A). Step 519 begins by extracting corresponding pixel values for one pixel from the current pixel block 700 and previous pixel block 701 (step 703). Then, the pixel color values are used to calculate a distance value, which indicates the magnitude of the similarity or difference between the colors of the two pixels (step 705). In the preferred embodiment of the present invention, the distance value is computed using the following formula:

$$D=(R1-R2)^2+(G1-G2)^2+(B1-B2)^2$$

As before, R1, G1, and B1 are the red, green and blue values respectively of the frame buffer pixel. Similarly, R2, G2, and B2 are the red, green and blue values respectively for the compare frame buffer pixel.

Next, the computed distance value D is compared with a pixel threshold (step 707). If D is greater than the pixel threshold, it is added to an accumulating distance sum (step 709). If the value of D is less than the pixel threshold, the difference is considered to be insignificant or noise and it is not added to the distance sum.

This process of computing distance values and summing distance values that are greater than a predefined pixel threshold continues until it is determined that the last pixel of the block of pixels has been processed (step 711). Once the last pixel is reached, the distance sum is compared with a second threshold, the block threshold (step 713). If the distance sum is greater than the block threshold, the current block of pixels designated as changed as compared to the corresponding block of pixels from the previously captured frame. Otherwise, if the distance sum is less than the block threshold, the block of pixels is designated as unchanged.

If the block of pixels is designated as changed, step 715 is executed. Step 715 sets a flag that indicates that the particular block of pixels has changed. Furthermore, the new block of pixels is written to compare frame buffer 521 (FIG. 4A) to replace the corresponding previous block of pixels.

Otherwise, if the distance sum does not exceed the block threshold, the block is designated unchanged and, a flag is set to indicate that this block of pixels does not need to be re-transmitted to the remote participation equipment (step 721). Rather, the remote participation equipment will recreate the portion of the video image represented by the block of pixels using the same block of pixels displayed for the previous frame of video. At this point, step 523 is executed, as discussed in greater detail above with respect to FIG. 4A.

Figure 7:
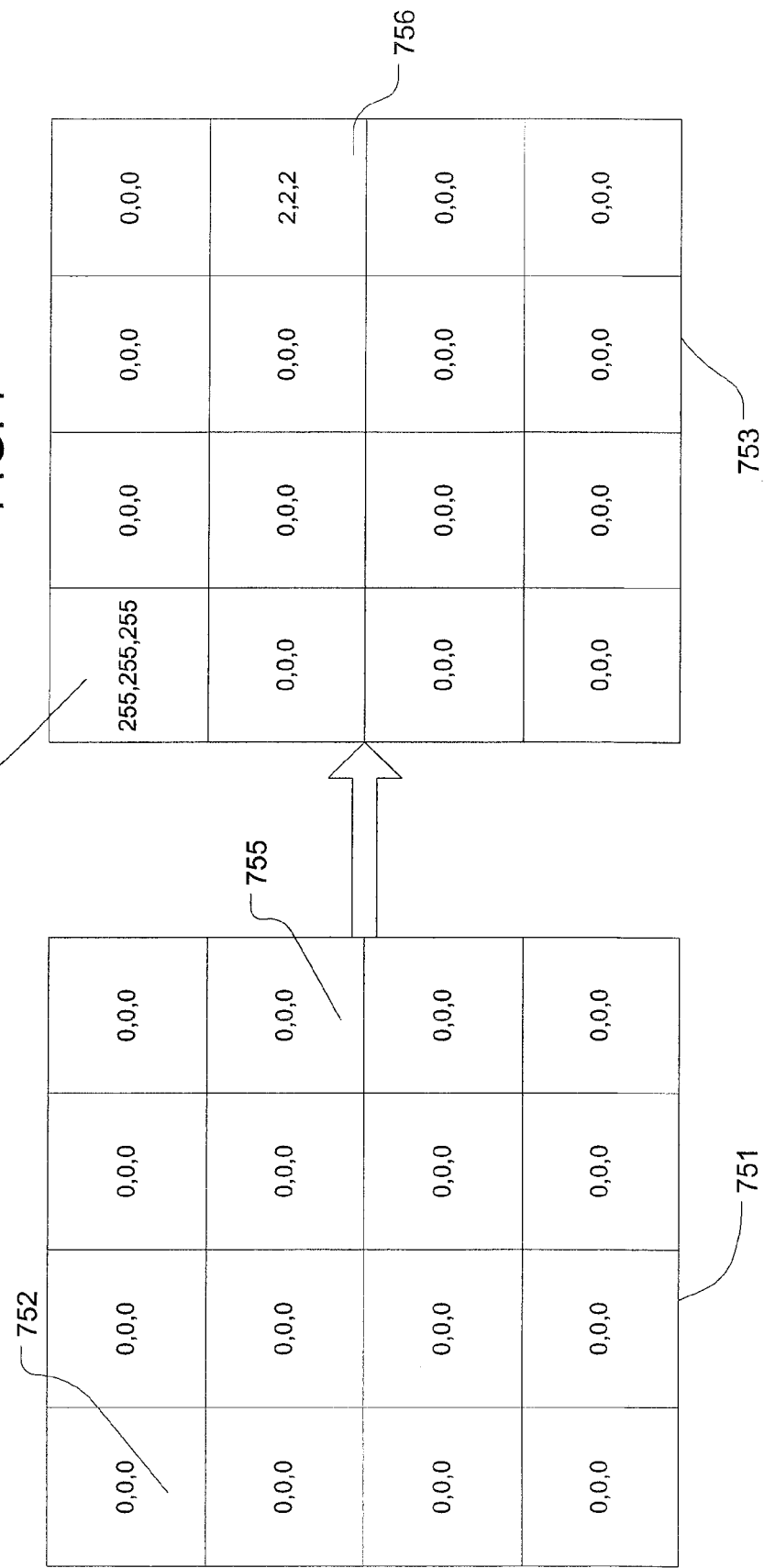
FIG. 7 depicts an example application of the NRDT sub-algorithm to a sample block of pixels as performed by the compression algorithm utilized by the preferred embodiment of the present invention.

FIG. 7 further illustrates the two level threshold algorithm utilized by the NRDT sub-algorithm of FIG. 6. For illustrative purposes, 4×4 blocks of pixels are shown. Each pixel is given red, green, and blue color values that range from 0 to 255, as is commonly performed in the art. A pixel having red, green, and blue values of 0 represents a black pixel, whereas a pixel having red, green, and blue values of 255 represents a white pixel. Previous pixel block 751 is a block of pixels grabbed from compare frame buffer 521 (FIG. 4A). Previous pixel 1 752 is the pixel in the upper, left corner of previous pixel block 751. Since every pixel of previous pixel block 751 has a value of 0, previous pixel block 751 represents a 4×4 pixel area that is completely black.

Current pixel block 753 represents the same spatial area of the video frame as previous pixel block 751, but it is one frame later. Here current pixel 1 754 is the same pixel 1 as previous pixel 1 752, however, it occurs one frame later. To simplify explanation, suppose a small white object, such as a white cursor, enters the area of the video image represented by previous pixel block 751. This change occurs in current pixel 1 754 of current pixel block 753. In current pixel block 753, the majority of the pixels remained black, however current pixel 1 754 is now white as represented by the RGB color values of 255, 255, and 255.

Further suppose that noise has been introduced by the A/D conversion, such that previous pixel 2 755 has changed from black, as represented by its RGB values of 0, 0, and 0, to gray. The new gray color is represented by the RGB values of 2, 2, and 2 assigned to current pixel 2 756.

Further suppose that the pixel threshold is 100, and the block threshold is 200. The NRDT sub-algorithm calculates the distance value between each pixel of current pixel block 753 and previous pixel block 751. The formula used in the preferred embodiment of the present invention, as discussed above with respect to FIG. 6, is:

$$D = (R1-R2)^2 + (G1-G2)^2 + (B1-B2)^2$$

Therefore, the distance value between current pixel 1 754 and previous pixel 1 752 is:

$$D = (255-0)^2 + (255-0)^2 + (255-0)^2$$

or 195,075. This distance value is added to the distance sum because 195,075 exceeds the pixel threshold of 100. However, the distance value between the black previous pixel 2 755 and the gray current pixel 2 756 is not added to the distance sum because the distance between the pixels, as calculated using the above distance formula, equals 12, which does not exceed the pixel threshold of 100. Similarly, the distance value is computed for all of the remaining pixels in the two pixel blocks. Each of these distance values equals zero, therefore, since these distance values are less than the pixel threshold, they are not added to the distance sum.

Consequently, after the distance values for all pixels have been processed, the distance sum equals 195,075. Since this value is greater than the block threshold of 200, the block is designated. This example illustrates the advantages of the two-level thresholding feature of the NRDT sub-algorithm. That is, the noise that occurred in current pixel 2 756 of current pixel block 753 was ignored, whereas the real change in video that occurred in current pixel 1 754 of current pixel block 753 was recognized.

Figure 8:
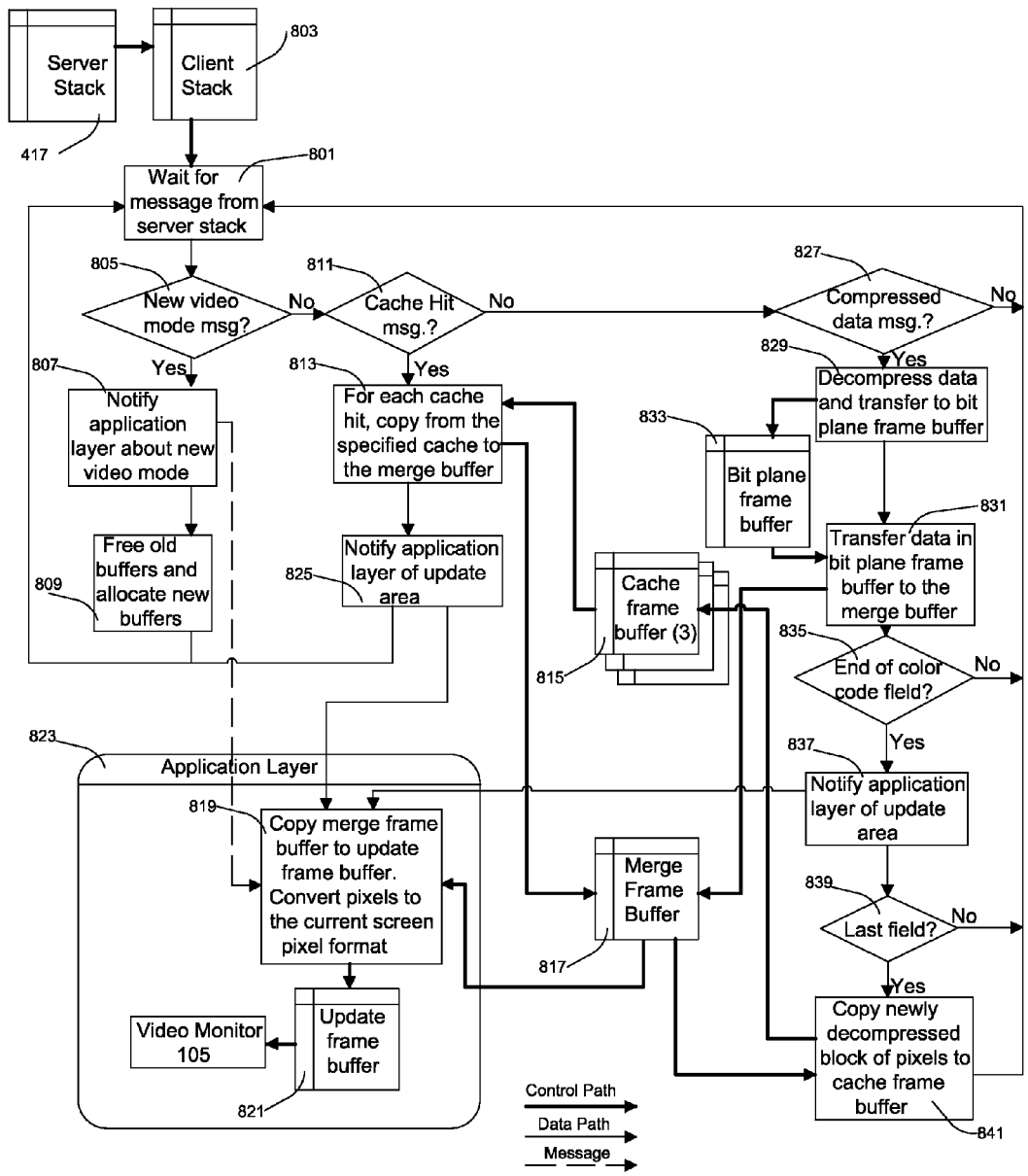
FIG. 8 depicts a detailed flowchart of the operation of the decompression algorithm used by the preferred embodiment of the present invention.

FIG. 8 is a flowchart of the decompression algorithm executed by user workstation 101 (FIG. 1). The decompression algorithm begins by waiting for a message (step 801). This message is transmitted from server stack 417 of RMU 109 to user workstation 101. Thereafter, user workstation 101 receives the information and writes the data to client stack 803. Client stack 803 may be a register or some other device capable of permanently or temporarily storing digital data. In one embodiment of the present invention, messages are transmitted using a TCP/IP communication protocol. In this scenario, client stack 803 is the local TCP/IP stack. Other embodiments may use a protocol other than TCP/IP, however, irrespective of the communication protocol, the present invention uses client stack 803 to store received messages for processing.

Once a message is received in client stack 803, it is processed to determine whether the message is a new video mode message (step 805). A new video mode message can be sent for a variety of reasons including a bandwidth change, a change in screen resolution or color depth, a new client, etc. This list is not intended to limit the reasons for sending a new video mode message, but instead to give examples of when it may occur. If the message is a new video mode message, application layer 823 is notified of the new video mode (step 807). In the preferred embodiment of the present invention, application layer 823 is software executed by user workstation 101 that interfaces with the input and output devices of user workstation 101 (i.e., keyboard 103, video monitor 105, and cursor control device 107). Any video updates must therefore be sent to application layer 823. Also, the old buffers are freed, including all memory devoted to storing previously transmitted frames, and new buffers are allocated (step 809). The decompression algorithm then returns to step 801.

If the new message is not a video mode message, the message is further processed to determine if it is a cache hit message (step 811). If yes, the cache hit message is deciphered to determine which block of pixels, of the blocks of pixels stored in the three cache frame buffers 815, should be used to reconstruct the respective portion of the video image.

Although three cache frame buffers 815 are used in the preferred embodiment of the present invention, any quantity of cache frame buffers may be used without departing from the spirit of the invention. Cache frame buffers 815 store the same blocks of pixels that are stored in the cache frame buffers located internal to RMU 109 (FIG. 2). Thus, the cache hit message does not include video data, rather, it simply directs the remote participation equipment as to which block of pixels contained in the cache frame buffer 815 should be sent to merge frame buffer 817. The block of pixels contained within the specified cache is then copied from cache frame buffer 815 to merge buffer 817 (step 813). Finally, application layer 823 is notified that an area of the video image has been updated (step 825). Merge buffer 817 contains the current representation of the entire frame of video in color code pixels. Application layer 823 copies the pixel data from merge buffer 817 and formats the data to match the pixel format of the connected video monitor 105 (step 819). Thereafter, the formatted pixel data is written to update frame buffer 821, which then transmits the data to video monitor 105. Alternatively, in lieu of a video monitor, the formatted pixel data may be written to a video card, memory, and/or any other hardware or software commonly used with video display devices.

Further, if the new message is not a new video mode or cache hit message, it is tested to determine if it is a message containing compressed video data (step 827). If the message does not contain compressed video data, the decompression algorithm returns to step 801 and waits for a new message to be transmitted from server stack 417. Otherwise, if the message does contain compressed video data, the data is decompressed and transferred to bit plane frame buffer 833 (step 829). As described above, the preferred embodiment of the present invention incorporates the JBIG lossless compression technique. Therefore, decompression of the video data must be performed for each individual bit plane. After each bit plane is decompressed, it is merged with previously decompressed bit planes, which are stored in bit plane frame buffer 833 (step 829). When a sufficient number of bit planes have been merged, the merged data contained in bit plane frame buffer 833 is transferred to merge frame buffer 817. Alternatively, individual bit planes may be decompressed and stored directly in merge frame buffer 817; thereby eliminating bit plane frame buffer 833 (step 831). When all of the data required to display a full frame of video is transferred to merge frame buffer 817, application layer 823 copies the data in merge frame buffer 817 to update frame buffer 821 (step 819). Thereafter, the data is transferred to video monitor 105.

In an alternate embodiment, the video displayed on video monitor 105 can be updated after each bit plane is received. In other words, a user does not have to wait until the whole updated frame of video is received to update portions of the displayed video. This alternative method is desirable when the bandwidth available for video transmission varies. Also, this progressive method of updating the video display is one of the advantages of using the JBIG compression algorithm.

Next, the decompression algorithm determines whether all of the color code data from one field of the current video frame has been received (step 835). If a full field has not been received, the decompression algorithm returns to step 801 and waits for the remainder of the message, which is transmitted from server stack 417 to client stack 803 in the form of a new message. Otherwise, if a full field has been received, the decompression method notifies application layer 823 (step 837). Similar to that described above with respect to processing cache hit messages, this notification directs application layer 823 to read the data in merge frame buffer 817 and convert it to the current screen pixel format (step 819). Thereafter, the formatted data is written to update frame buffer 821, which transmits the data to video monitor 105.

After a full field has been received and application layer 823 has been notified, a second determination is made to determine if the full field is the last field included in the message. If it is, the newly decompressed block of pixels is written to one of the cache frame buffers 815 (step 841). Otherwise, the decompression algorithm returns to step 801 and continues to wait for a new message. In the preferred embodiment of the present invention, the new block of pixels written to cache frame buffer 815 overwrites the oldest block of pixels contained therein. Step 841 ensures that the cache is up-to-date and synchronized with the cache of RMU 109. After the completion of the cache update, the decompression algorithm returns to step 801.

While the present invention has been described with reference to the preferred embodiments and several alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

I claim:

1. A Keyboard, Video, Mouse ("KVM") system with improved video digitization and image correction, said KVM system comprising:
 a remote management unit;
 a plurality of workstations each containing at least a keyboard or cursor control device, wherein the plurality of workstations are coupled to the remote management unit via a first communications medium,
 a plurality of remote networking devices coupled to the remote management unit via a second communications medium;
 wherein the remote management unit includes:
 a Liquid Crystal Display ("LCD") controller comprising an analog-to-digital ("A/D") converter, the LCD controller for converting analog video signals received from at least one of the remote networking devices to image-correction processed digital video signals,
 a video processor circuit for compressing said image-correction processed digital video signals,
 a packetizer for packetizing the compressed, image-correction processed digital video signals, and
 modules for processing and bidirectionally communicating over the first communications medium keyboard and cursor control signals to and from the plurality of workstations and for transmitting the packetized, compressed, image-correction processed digital signals to the plurality of workstations via the first communication medium, and
 wherein all keyboard and cursor control device signals bidirectionally pass through the LCD controller unprocessed.

2. The system according to claim 1, wherein said first communications medium is at least one selected from the group consisting of a LAN, a WAN, a wireless connection, a modem, a direct modem connection, and the Internet.

3. The system according to claim 1, wherein the second communications medium comprises cabling between each of the plurality of remote networking devices and the remote management unit through cabling via a port selected from the group consisting of a serial port, parallel port, keyboard port, video port, cursor control device port, USB port, firewire port, blue tooth port, Ethernet port, and a power supply port.

4. The system according to claim 1, wherein said remote management unit controls access by requiring identification data to authenticate a user.

5. The system according to claim 1, wherein said remote management unit and said plurality of user workstations communicate via Clip.

6. The system according to claim 1, wherein said remote management unit and said plurality of user workstations communicate via the Internet.

7. The system according to claim 1, wherein said LCD controller includes an input interface circuit for detecting a color palette utilized by said remote network device.

8. The system according to claim 1, wherein said LCD controller includes a synchronization selector circuit for receiving horizontal and vertical synchronization signals.

9. The system according to claim 8, wherein said LCD controller includes a mode detection circuit for receiving said synchronization signals from said synchronization selector circuit and for determining a frequency of said synchronization signals.

10. The system according to claim 1, wherein said LCD controller includes an auto-adjustment circuit for performing at least one of active area detection, pixel brightness searching and phase distortion measurement.

11. The system according to claim 10, wherein said auto-adjustment circuit updates timing of a clock during said phase distortion measurement.

12. The system according to claim 1, wherein said LCD controller includes a downscaler circuit for reducing high video resolution to low video resolution.

13. The system according to claim 1, wherein said LCD controller includes an upscaler circuit for increasing low video resolution to high video resolution.

14. The system according to claim 1, wherein said LCD controller includes an option menu circuit for enabling a user to select one of a plurality of serial devices, remote servers, remote computers or power devices.

15. The system according to claim 1, wherein said LCD controller modifies each pixel of said digital video signals according to a color palette.

16. The system according to claim 1, wherein said LCD controller includes a dithering circuit for approximating a color for a pixel of said digital video signals.

17. The system according to claim 1, wherein said LCD controller includes an output interface circuit for adjusting timing of said analog video signals.

18. The system according to claim 1, wherein said video processor circuit includes a pixel receiving circuit for receiving pixel information from said digital video signals.

19. The system according to claim 18, wherein said video processor circuit includes a frame buffer circuit for storing said pixel information.

20. The system according to claim 1, wherein said video processor circuit includes a video compression circuit.

21. The system according to claim 1, wherein said LCD controller converts said digital video signals for compatibility with a video display of one of said plurality of workstations.

22. A method for providing improved video digitization and image correction in a KVM system, said method comprising the steps of:

receiving analog video signals and control signals from one of a plurality of remote devices connected to a remote management unit;

processing the received analog video signals using an analog-to-digital ("A/D") converter element of an LCD controller to convert the analog video signals to digital video signals;

correcting the digital video signals by the LCD controller to form image-correction processed digital video signals;

passing the control signals to and from one of the plurality of remote devices through the LCD controller unprocessed and uncorrected;

compressing the image-correction processed digital video signals by a video processor circuit;

packetizing the compressed, image-correction processed digital video signals by a packetizer, and transmitting the packetized, compressed image-correction processed digital video signals and the control signals to one of a plurality of user interface devices.

23. The method according to claim 22, wherein said user interface devices are accessible by inputting unique authentication information.

24. The method according to claim 22, further comprising the step of:

displaying said digital video signals on a video display of one of said user interface devices.

25. The method according to claim 22, wherein a compression algorithm is used to perform said compressing.

26. The method according to claim 25, wherein said compression algorithm determines noise in said digital video signals, smoothes said digital video signals, determines changes to pixels of said digital video signals, and compresses said changed digital video signals.

27. The method according to claim 22, wherein said transmitting occurs via TCP/IP.

28. The method according to claim 22, wherein said correcting comprises image correction.

29. The method according to claim 28, wherein said image correction includes detecting a color palette of said digital video signals.

30. The method according to claim 22, wherein said correcting includes receiving horizontal and vertical synchronization signals.

31. The method according to claim 22, wherein said correcting includes determining one or more frequencies of said digital video signals.

32. The method according to claim 22, wherein said correcting includes detecting an active area of a video image represented by said digital video signals.

33. The method according to claim 22, wherein said correcting includes determining brightness of each pixel of said digital video signals.

34. The method according to claim 22, wherein said correcting includes measuring phase distortion of said digital video signals.

35. The method according to claim 22, wherein said correcting includes measuring one or more pixels of said digital video signals.

36. The method according to claim 22, wherein said correcting includes reducing high video resolution to low video resolution.

37. The method according to claim 22, wherein said correcting includes increasing low video resolution to high video resolution.

38. The method according to claim 22, wherein said correcting includes dithering said digital video signals.

39. The method according to claim 22, wherein said correcting includes adjusting timing of said digital video signals.

40. The method according to claim 22, wherein said method further comprises the step of: storing pixel information of digital video signals.

\* \* \* \* \*